United States Patent [19]

Postlethwaite et al.

[11] Patent Number: 5,436,228

[45] Date of Patent: Jul. 25, 1995

[54] CHEMOTACTIC WOUND HEALING PEPTIDES

[76] Inventors: Arnold E. Postlethwaite, 635 Bethany Rd., Eads, Tenn. 38028; Jerome Seyer, 1412 Carr Ave., Memphis, Tenn. 38104; Andrew Kang, 2334 Massey Rd., Memphis, Tenn. 38119

[21] Appl. No.: 127,909

[22] Filed: Sep. 28, 1993

Related U.S. Application Data

[63] Continuation-in-part of Ser. No. 626,631, Dec. 12, 1990, abandoned.

[51] Int. Cl.$^6$ .............. A61K 38/00; C07K 5/00; C07K 7/00; C07K 17/00
[52] U.S. Cl. .................... 514/12; 514/13; 514/14; 514/16; 530/324; 530/326; 530/329
[58] Field of Search .................. 514/12–14, 514/16; 530/324, 326, 329

[56] References Cited

U.S. PATENT DOCUMENTS

| | | | |
|---|---|---|---|
| 4,806,523 | 2/1989 | Bentz et al. | 514/2 |
| 4,971,952 | 11/1990 | Bentz et al. | 514/12 |
| 5,008,240 | 4/1991 | Bentz et al. | 514/2 |
| 5,055,447 | 10/1991 | Palbdino | 514/12 |
| 5,061,786 | 10/1991 | Burnier et al. | 530/326 |
| 5,104,977 | 4/1992 | Sporn et al. | 530/399 |

FOREIGN PATENT DOCUMENTS

| | | |
|---|---|---|
| 0542679 | 5/1993 | European Pat. Off. . |
| 2152988 | 8/1988 | Japan . |
| US90/05091 | 3/1991 | WIPO . |
| US90/06006 | 5/1991 | WIPO . |

OTHER PUBLICATIONS

Jakowlew et al. Mol. Endo vol. 2 p. 1186 (1988).
Kondaiah et al. J. Biol. Chem. vol. 265, p. 1089 (1990).
Duke et al. PNAS, USA vol. 85 p. 4715 (1988).
Margvaudt et al. J. Biol. Chem. vol. 262 p. 1212t (1987).
Border et al., 1992 Tansforming Growth Factor-β in Disease: The Dark Side of Tissue Repair. *J. Clin. Invest.*, 90:1–7.
Davidson, J. M., 1992 Wound Repair. Inflammation: Basic Principles and Clinical Correlates, 2d ed., J. I. Gallin, I. M. Goldstein and R. Snyderman, eds., Raven Press, Ltd., New York chapter 39 pp. 809–819.
Flanders et al., 1988 Antibodies to Peptide Determinants in Transforming Growth Factor β and Their Applications. *Biochem.* 27:739–746.
Massague et al., 1992 Transforming Growth Factor-β. Cancer Surveys vol. 12: Tumour Suppressor Genes, the Cell Cycle and Cancer, pp. 81–103.
Postlethwaite et al., 1992 Identification of Chemotactic Epitopes of Transforming Growth Factor (TGF)-β1. Arthritis and Rhumatism vol. 35, No. 9, Supplement (Abstract A62).
Postlethwaite, A., 1993 Stimulation of Elevated levels of IL-1β Protein and IL-1β mRNA by Snythetic TGF-β1 Peptide, 337–374. ACR 57th Annual Scientific Meeting, San Antonio, Tex. (Abstract).
Postlethwait4e et al., 1987 Stimulation of the Chemotactic Migration of Human Fibroblasts by Transforming Growth Factor β. *J. Exper. Med.*, 165:251–256.
Sasaki et al., 1992 Transforming Growth Factor-β in the Regulation of the Immune Response. *Clinical Immunology and Immunopathology.* vol. 65, 1:1–9.

*Primary Examiner*—Jill Warden
*Assistant Examiner*—Sheela J. Huff
*Attorney, Agent, or Firm*—Scully, Scott, Murphy & Presser

[57] ABSTRACT

Peptides corresponding to an no acid sequences in the C-terminal region of TGF-β are provided. The peptides all contain at least a seven amino acid sequence substantially corresponding to the amino acid sequence of TGF-β1 amino acids 368–374: VYYVGRK, as well as homologs and analogs thereof. The peptides have chemotactic activity towards fibroblasts, monocytes and neutrophils and induce fibroblast proliferation and collagen synthesis. The peptides may be used in compositions and methods for promoting wound healing.

14 Claims, 13 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Val  Tyr  Tyr  Val  Gly  Arg  Lys
    1                      5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Leu  Tyr  Tyr  Ile  Gly  Lys  Thr
1                   5
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Leu  Tyr  Tyr  Val  Gly  Arg  Thr
1                   5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ile  Tyr  Tyr  Val  Gly  Arg  Asn
1                   5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Ile  Tyr  Tyr  Val  Gly  Arg  Thr
1                   5
```

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Pro  Leu  Pro  Ile  Val  Tyr  Tyr  Val  Gly  Arg  Lys  Pro  Lys  Val  Glu
1                   5                        10                       15
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear (i) MOLECULE TYPE: peptide (xi) SEQUENCE DESCRIPTION: SEQ ID NO:7:

```
Pro Leu Thr Ile Leu Tyr Tyr Ile Gly Lys Thr Pro Lys Ile Glu
1               5                   10                  15
```

(2) INFORMATION FOR SEQ ID NO:8:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:8:

```
Pro Leu Thr Ile Leu Tyr Tyr Val Gly Arg Thr Pro Lys Val Glu
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:9:

```
Pro Leu Pro Ile Ile Tyr Tyr Val Gly Arg Asn Val Arg Val Glu
1               5                   10                  15
```

(2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:10:

```
Pro Leu Pro Ile Ile Tyr Tyr Val Gly Arg Thr Ala Lys Val Glu
1               5                   10                  15
```

(2) INFORMATION FOR SEQ ID NO:11:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:11:

```
Pro Ile Val Tyr Tyr Val Gly Arg Lys Pro Lys Val Glu Gln Leu Ser
1               5                   10                  15
Asn Met Ile Val Arg Ser
                20
```

(2) INFORMATION FOR SEQ ID NO:12:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:12:

-continued

```
Thr Ile Leu Tyr Tyr Ile Gly Lys Thr Pro Lys Ile Glu Gln Leu Ser
1               5                   10                  15

Asn Met Ile Val Lys Ser
                20
```

(2) INFORMATION FOR SEQ ID NO:13:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:13:

```
Thr Ile Leu Tyr Tyr Val Gly Arg Thr Pro Lys Val Glu Gln Leu Ser
1               5                   10                  15

Asn Met Val Val Lys Ser
                20
```

(2) INFORMATION FOR SEQ ID NO:14:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:14:

```
Pro Ile Ile Tyr Tyr Val Gly Arg Asn Val Arg Val Glu Gln Leu Ser
1               5                   10                  15

Asn Met Val Val Arg Ala
                20
```

(2) INFORMATION FOR SEQ ID NO:15:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:15:

```
Pro Ile Ile Tyr Tyr Val Gly Arg Thr Ala Lys Val Glu Gln Leu Ser
1               5                   10                  15

Asn Met Val Val Arg Ser
                20
```

(2) INFORMATION FOR SEQ ID NO:16:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:16:

```
Val Pro Gln Ala Leu Glu Pro Leu Pro Ile Val Tyr Tyr Val Gly Arg
1               5                   10                  15

Lys Pro Lys Val Glu Gln Leu Ser Asn
                20                  25
```

(2) INFORMATION FOR SEQ ID NO:17:

(i) SEQUENCE CHARACTERISTICS:

(A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:17:

Val Ser Gln Asp Leu Glu Pro Leu Thr Ile Leu Tyr Tyr Ile Gly Lys
 1           5                  10                  15

Thr Pro Lys Ile Glu Gln Leu Ser Asn
            20                  25

(2) INFORMATION FOR SEQ ID NO:18:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:18:

Val Pro Gln Asp Leu Glu Pro Leu Thr Ile Leu Tyr Tyr Val Gly Arg
 1           5                  10                  15

Thr Pro Lys Val Glu Gln Leu Ser Asn
            20                  25

(2) INFORMATION FOR SEQ ID NO:19:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:19:

Val Pro Gln Thr Leu Asp Pro Leu Pro Ile Ile Tyr Tyr Val Gly Arg
 1           5                  10                  15

Asn Val Arg Val Glu Gln Leu Ser Asn
            20                  25

(2) INFORMATION FOR SEQ ID NO:20:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:20:

Val Pro Gln Val Leu Glu Pro Leu Pro Ile Ile Tyr Tyr Val Gly Arg
 1           5                  10                  15

Thr Ala Lys Val Glu Gln Leu Ser Asn
            20                  25

CHEMOTACTIC WOUND HEALING PEPTIDES

CROSS REFERENCE TO RELATED APPLICATIONS

This application is a continuation-in-part of U.S. patent application Ser. No. 626,631, filed Dec. 12, 1990, now abandoned. The invention disclosed herein was made during the course of a grant funded by the United States government and is thus subject to the rights of the government therein.

TECHNICAL FIELD

The present invention relates to protein and peptide chemistry. More particularly, it relates to the discovery and isolation of novel peptides whose sequences correspond to regions of the amino acid sequence of various transforming growth factor $-\beta$ ("TGF-$\beta$") polypeptides that have chemotactic properties. The invention is also directed toward the use of these novel peptides which provide a chemotactic stimulus towards inflammatory cells, such as neutrophils and monocytes, and fibroblasts, induce fibroblast proliferation and stiumlate collagen production to promote wound healing in animals and man.

BACKGROUND

Transforming growth factors ("TGFs") are polypeptides that, in certain nontumorigenic cell types, reversibly induce features resembling those of malignant transformation. Two distinct types of TGFs are known—TGF-$\alpha$ and TGF-$\beta$. TGF-$\alpha$ is related to epidermal growth factor (EGF) and binds to the same cellular receptors as EGF.

TGF-$\beta$s, which have been found in a variety of cells, including T-lymphocytes, monocytes and platelets, are structurally and antigenically distinct from TGF-$\alpha$ and comprise a group of closely related paracrine factors that elicit a variety of biological effects. Cellular responses to TGF-$\beta$s may be grouped into three main categories: proliferative responses; effects on cell differentiation and differentiated functions; and responses involving cell adhesion, migration and extracellular matrices.

In most cases, TGF-$\beta$s inhibit cellular proliferation. TGF-$\beta$s are also known to regulate differentiation of myoblasts, osteoblasts, chondroblasts, preadipocytes, hematopoietic progenitors and other cells. Depending on the type or lineage of specific cells, such regulation may either favor or reversibly inhibit differentiation. For example, TGF-$\beta$s can regulate the specialized functions of lymphocytes and hormone production by adrenocortical, granulosa and pituitary cells.

TGF-$\beta$s can also produce alterations in the extracellular matrix or autocrine cytokine production that may play a role in the physiological action of these polypeptides in tissue morphogenesis, remodelling and repair, including wound healing. See, e.g., U.S. Pat. No. 5,104,977. Moreover, TGF-$\beta$ are known to stimulate fibronectin and. collagen production by dermal fibroblasts in vitro.

The in vivo administration of TGF-$\beta$ to newborn mice was shown to induce a rapid fibrotic response and accumulation of fibroblasts into the injection site. More recently, platelet-derived TGF-$\beta$ was shown to be a potent chemoattractant for fibroblasts in vitro. (Postlewaite, A. et al., J. Exptl. Med. 165:251–256, 1987). The ability of TGF-$\beta$ to be a chemoattractant for fibroblasts and inflammatory cells, e.g., neutrophils and monocytes/macrophages has led to the finding that this cytokine apparently plays important roles in wound healing and tissue repair. (See Davidson, J. M., in *Inflammation: Basic Principals and Clinical Correlates*, Second Edition, Gallin, Goldstein and Snyderman, eds., Raven Press, 11992, pp. 809–819, for review). For example, PCT WO 84/001106, filed Sep. 23, 1983, describes TGF-$\beta$1 and its use in promoting cell proliferation, tissue repair, wound healing and treatment of trauma. See also U.S. Pat. No. 5,104,977.

Structurally, TGF-$\beta$s are disulfide-linked 25 kDa dimeric proteins, with the mature monomeric polypeptide comprising 112 amino acids. The mature chain is derived from a larger precursor comprising approximately 390–412 amino acids (Derynck et al., Nature 316:710–705, 1985; Massague, J. et al., *Cancer Surveys* Volume 12: *Tumor Suppressor Genes, the Cell Cycle and Cancer*, pp. 81–103, 1992). The biologically active mature polypeptide chain is derived from the carboxyterminus of the precursor. Apparently, proteolytic cleavage to the mature protein occurs intracellularly, after dimerization of the precursor.

There are at least five known isoforms of TGF-$\beta$ (designated TGF-$\beta$1-5), which are about 70% homologous in amino acid sequence to each other. At least three genes (apparently located on different chromosomes) encode the TGF-$\beta$1, $\beta$2 and $\beta$3 precursors in the human and other mammalian genomes. Two additional TGF genes, coding for TGF-$\beta$4 and TGF-$\beta$5, have been identified in chicken and *Xenopus laevis* genomes, respectively. The degree of amino acid sequence homology between $\beta$1, $\beta$2 and $\beta$3 polypeptide chains is about 70% (range 64–82%). On the other hand, the amino acid sequence of each TGF-$\beta$ isoform is strictly conserved, with the sequence homology of, e.g., $\beta$1 being nearly 100% between the chicken and human polypeptides (similar homologies have been observed for $\beta$2 and $\beta$3 between chicken and human).

Generally, the constituent polypeptide chains form homodimers to yield TGF-$\beta$1, $\beta$2 and $\beta$3 proteins, respectively. Heterodimers, however, may be formed in some cells which simultaneously express different TGF-$\beta$ genes, e.g., porcine megakaryocytes, to yield platelets containing TGF-$\beta$1.2 heterodimers, in addition to homodimers.

As discussed above, TGF-$\beta$1 has proved to be a potent chemotactic agent for cells of mesenchymal origin, e.g., fibroblasts and inflammatory cells, including neutrophils and monocytes/macrophages. In large part because of its activity as a chemoattractant, TGF-$\beta$1 is believed to play a critical role in inflammatory and tissue repair processes, including wound healing. The recruitment of inflammatory cells to the site of a wound is necessary for proper tissue repair. Likewise, the recruitment and subsequent proliferation of fibroblasts, which initiate a fibrogenic response, are also required. Prior to the present work, however, it was unknown what structural features of TGF-$\beta$1 (or the other TGF-$\beta$s) would be involved in the ability of the peptide to cause chemotaxis of cells. Accordingly, the present invention provides novel peptides corresponding to the amino acid sequence of TGF-$\beta$s that are chemotactic for fibroblasts and inflammatory cells and may be used in wound healing and tissue repair compositions.

DISCLOSURE OF THE INVENTION

In accordance with the present invention, a number of novel chemotactic peptides, derived from TGF-βs, have been made by solid phase peptide synthesis. These peptides possess chemoattractant properties for fibroblasts and inflammatory cells, including neutrophils and monocytes/macrophoges.

Moreover, the peptides of the present invention also appear to stimulate fibroblast proliferation and collagen synthesis.

The peptides according to the present invention all comprise at least a seven amino acid sequence derived from the carboxyl terminal portion of TGF-β, corresponding to amino acids 368-374 of TGF-β1. The amino acid sequence numbering of TGF-β1 (and by homology, the other TGF-β) herein follows that of Derynck et al., Nature 316:701 (1985).

Larger peptides of 15, 22 and 25 amino acids in length, each containing within its sequence the aforementioned seven amino acid peptide are also part of the present invention.

In a preferred embodiment, the amino acid sequences of the chemotactic peptides substantially correspond to amino acid residues 368-374 of TGF-β1 (See, e.g., SEQ ID NO. 1), as well as sequence of homologs and analogs thereof. By homologs is meant the corresponding peptides (See SEQ ID NOs. 2-5) derived from other known TGF-βs1 having the same or substantially the same chemotactic and other properties as the prototype TGF-β1 peptide. By analogs is meant substitutions in the amino acid sequence of the peptides, so long as the chemotactic and, fibrogenic, etc. properties of the peptides are retained. Analogs may also encompass additional amino acids, added to the N- and/or C-terminal portion of the peptide. For example, analogs of the peptides of the invention may contain cysteine or another amino acid, at the amino or carboxyl end of the peptide by which the peptide may be covalently attached to a carrier protein, e.g. albumin, for in vivo administration.

In a second embodiment, the peptides of the present invention have amino acid sequences substantially corresponding to amino acids 364-378 of TGF-β1 (See, SEQ. ID NOs. 6-10), as well as homologs and analogs thereof.

In a further embodiment, the peptides of the invention have amino acid sequences substantially corresponding to amino acids 366-387 of TGF-β1 (See SEQ ID. NOs. 16-20), as well as homologs and analogs thereof.

In a still further embodiment, the peptides of the invention have an amino acid sequence substantially corresponding to amino acids 358-382 of TGF-β1, as well as homologs and analogs thereof.

In another embodiment of the invention, the chemotactic peptides of the invention substantially correspond to the following amino acid sequences:

(A) V Y Y V G R K,
    L Y Y I G K T,
    L Y Y V G R T,
    I Y Y V G R N, and
    I Y Y V G R T;
(B) P L P I V Y Y V G R K P K V E,
    P L T I L Y Y I G K T P K I E,
    P L T I L Y Y V G R T P K V E,
    P L P I I Y Y V G R N V R V E, and
    P L P I I Y Y V G R T A K V E;
(C) P I V Y Y V G R K P K V E Q L S N M I V R S,
    T I L Y Y I G K T P K I E Q L S N M I V K S,
    T I L Y Y V G R T P K V E Q L S N M V V K S,
    P I I Y Y V G R N V R V E Q L S N M V V R A,
    and
    P I I Y Y V G R T A K V E Q L S N M V V R S;
(D) V P Q A L E P L P I V Y Y V G R K P K V E Q L S N,
    V S Q D L E P L T I L Y Y I G K T P K I E Q L S N,
    V P Q D L E P L T I L Y Y V G R T P K V E Q L S N,
    V P Q T L D P L P I I Y Y V G R N V R V E Q L S N,
    and
    V P D V L E P L P I I Y Y V G R T A K V E Q L S N;

as well as homologs and analogs thereof; wherein
A=Ala=Alanine
R=Arg=Arginine
N=Asn=Asparagine
D=Asp=Aspartic acid
B=Asx=Asparagine or aspartic acid
C=Cys=Cysteine
Q=Gln=Glutamine
E=Glu=Glutamic acid
Z=Glx=Glutamine or glutamic acid
G=Gly=Glycine
H=His=Histidine
I=Ile=Isoleucine
L=Leu=Leucine
K=Lys=Lysine
M=Met=Methionine
F=Phe=Phenylalanine
P=Pro=Proline
S=Ser=Serine
T=Thr=Threonine
W=Trp=Tryptophan
Y=Tyr=Tyrosine
V=Val=Valine The sequences of the peptides listed under (A), (B), (C) and (D) above are set forth as SEQ ID NOs. 1-5, 6-10, 11-15 and 16-20, respectively.

A further aspect of the invention is a chemotactic peptide of 7 to 25 amino acids substantially corresponding to the amino acid sequence of TGF-β1 and containing the amino acid sequence

V Y Y V G R K   SEQ ID NO. 1 as well as homologs and analogs thereof.

By "substantially corresponding" is meant an amino acid sequence having a homology to any of the listed sequences of about 70%.

The invention also provides compositions for the promotion of chemotaxis and proliferation of cells, primarily fibroblasts and inflammatory cells, in animals, including man. The compositions have as their active ingredients, at least one of the above peptides according to the present invention, admixed with a physiologically acceptable carrier.

The compositions may be formulated in any suitable carrier for topical application, such as physiological saline solution and purified collagen suspension. Alternatively, the composition may be incorporated into surgical or other surface dressings for topical administration. The compositions may also be formulated in any suitable carrier for systemic administration.

Topical administration of the compositions of the invention may be accomplished by methods involving direct application to a wound, burn or other surface trauma. Periodic or continued further application of the compositions to the trauma site is preferably indicated in most instances, since the active ingredients are physiologically active substances that may diffuse away from the site of application, be physiologically utilized by the cells being attracted to the site via the chemoattractant properties of the active agents and proliferate in response thereto, or may be degraded.

The compositions of the present invention may also be administered systemically by injection, internally, via transdermal patches and the like, depending upon the nature and site where tissue repair is required.

These and other embodiments of the invention will be readily apparent to those of ordinary skill in view of the disclosure herein.

DETAILED DESCRIPTION OF THE INVENTION

Figure 1A:
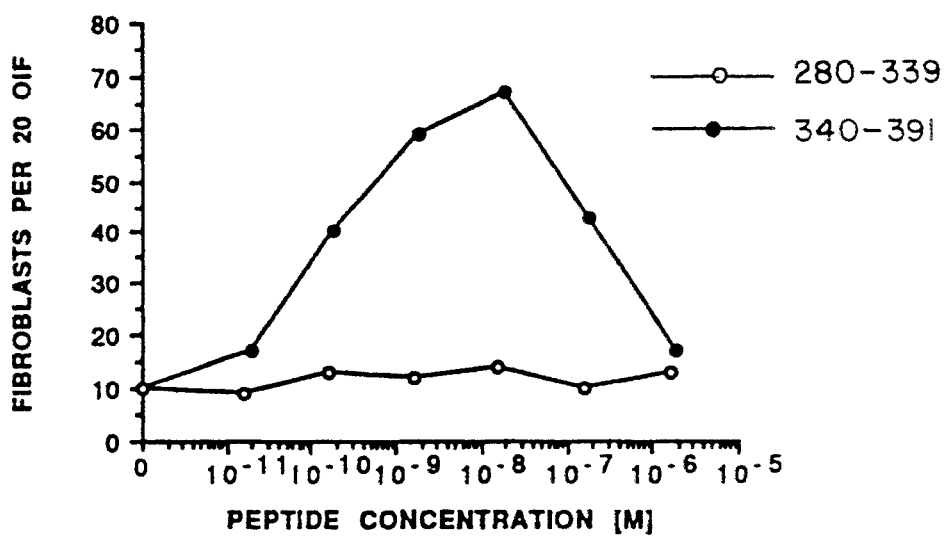
FIG. 1 is a graph comparing chemotaxis of fibroblasts, monocytes and neutrophils in response to peptides 340–391 and 280–339 corresponding to TGF-$\beta$1.

The present invention provides for a number of chemotactic peptides of 7–25 amino acids in length, which substantially correspond in sequence to amino acid sequence found in the carboxy-terminal portion of TGF$\beta$s. The prototype sequences of the peptides of the invention are derived from the amino acid sequence of TGF-$\beta$1, however, homologous peptides derived from TGF-$\beta$2, -$\beta$3, -$\beta$4 and -$\beta$5 are also encompassed by the invention. It is known that the various TGF-$\beta$ isoforms (i.e., $\beta$1–$\beta$5) are substantially homolgous in amino acid sequence, with the homology being about 70%. Thus, at a minimum, the longer peptides specifically disclosed herein, i.e., those of 15, 22 and 25 amino acids in length, all comprise the seven amino acid peptide sequence corresponding to amino acids 368–374 of TGF-$\beta$. Analogs of the peptides are also encompassed by the invention. By analogs is meant substitutions or alterations in the amino acid sequence of the peptides of the invention, which substitutions or alterations do not abolish the chemotactic or other biological properties of the peptides. Analogs also include the presence of additional amino acids added to either end of the peptides, which do not affect biological activity. For example, analogs of the peptides may contain an N- or C-terminal cysteine, by which, if desired, the peptide may be covalently attached to a carrier protein, e.g. albumin. Such attachment, it is believed, will minimize diffusion in vivo of the peptide from the site of application.

The practice of the present invention employs, unless otherwise indicated, conventional techniques of synthetic organic chemistry, protein chemistry, molecular biology, microbiology, and recombinant DNA technology, which are within the skill of the art. Such techniques are explained fully in the literature. See, e.g., Scopes, R. K., *Protein Purification Principles and Practices*, 2d ed. (Springer-Verlag, 1987), *Methods in Enzymology* (S. Colowick and No. Kaplan, eds., Academic Press, Inc.), Sambrook et al., *Molecular Cloning: A Laboratory Manual*, 2d ed., Cold Spring Harbor Press, Cold Spring Harbor, N.Y., 1989, *Handbook of Experimental Immunology*, Vols. I-IV (D. M. Weir and C. C. Blackwell, eds., 1986, Blackwell Scientific Publications); House, *Modern Synthetic Reactions*, 2d ed., Benjamin/-Cummings, Menlo Park, Calif., 1972.

As used herein, the term "peptide" refers to an oligomer of at least two contiguous amino acids.

Also, as used herein, "substantially corresponds" means a peptide amino acid sequence having an approximately 70% homology in amino acid sequence to a TGF-$\beta$ peptide.

The peptides of the invention, homologs and analogs thereof may be synthesized using classical Merrifield synthesis techniques. Oligopeptides were chemically synthesized by the solid phase method of Merrifield with,the aid of a Beckman (model 990) automated peptide synthesizer. Protected tBoc amino acids were purchased from Peninsula Laboratories, Inc. (Belmont, Calif.). [$^{14}$C]-labelled tBoc amino acids (New England Nuclear) were coupled sequentially to a benzyhydramine resin. Deprotection was achieved with trifluoroacetic acid (25% in dichloromethane), and coupling was obtained in the presence of dicyclohexylcarbodiimide. Completion of the coupling reaction was checked with ninhydrin using the Kaiser test. The complete peptide was cleaved from the resin, and the side-chain protecting groups removed by treatment with liquid hydrofluoric acid plus anisol at 0° C. The desired peptide was initially purified by filtration through a Sephadex G-25 column (4.0×60 cm) equilibrated with 0.1M acetic acid and 10–20% acetonitrile. The effluent was collected in fractions of 10 ml and aliquots taken for fluorescamine analysis. Fractions containing the peptide were pooled and lyophilized. Peptides were further purified by reverse phase HPLC. Separations were obtained by using a Beckman HLPC system and a Whatman ODS-3 (1-25 cm) semipreparative column. Buffer A was 0.05% trifluoroacetic acid and Buffer B was 0.05% trifluoroacetic acid in 60% acetonitrile with a flow rate of 2.0 ml/min. The gradient consisted of 20% Buffer B initially, 20-50% Buffer B in 45 minutes, and back to 20% Buffer B for 20 minutes. Amino acid composition of the final peptide was determined with a Beckman 121MB automatic amino acid analyzer, and the amino acid sequences confirmed by automatic Edman degradation using a Beckman 80 System or an Applied Biosystems 470A.

For longer peptides (up to 60 residues), an Applied Biosystems Peptide Synthesizer (Model 430 A) which utilizes symmetric anhydride coupling to the free amino group of the growing peptide chains with greater coupling efficiency was used. Except for the utilization of the phenylacetamidomethyl (PAM) resin to extend the growing polypeptide chain, the remaining methodologies are as above.

The amino acid sequences of the peptides were confirmed by amino acid composition analysis as well as manual and automated Edman degradation and determination of each amino acid.

In the amino acid sequences defined below, the numbering of the amino acid residues corresponds to the numbering of the amino acid residues in the amino acid sequence for human TGF-B1 provided in Derynck et al., Nature 316:710, 1985. Homologous peptides are derived from the homologous regions of the other TGF-βs, aligned in sequence for maximal homology. As noted, the different TGF-βisoforms (i.e., β1-5) are about 70% homologous in sequence to one another, while the same isoform (e.g., TGF-β1) has nearly 100% homology across species:

(A) Peptides 368-374 have the following sequences (also listed below as SEQ ID NOs. 1-5):

VYYVGRK,
LYYIGKT,
LYYVGRT,
IYYVGRN, and
IYYVGRT;

(B) Peptides 364-378 have the following sequences (also listed below as SEQ ID NOs. 6-10):

PLPIVYYVGRKPKVE,
PLTILYYIGKTPKIE,
PLTILYYVGRTPKVE,
PLPIIYYVGRNVRVE, and
PLPIIYYVGRTAKVE;

(C) Peptides 366-387 have the following sequences (also listed below as SEQ ID NOs. 11-15):

PIVYYVGRKPKVEQLSNMIVRS,
TILYYIGKTPKIEQLSNMIVKS,
TILYYVGRTPKVEQLSNMVVKS,
PIIYYVGRNVRVEQLSNMVVRA,
and
PIIYYVGRTAKVEQLSNMVVRS;

(D) Peptides 358-382 have the following sequences (also listed below as SEQ ID NOs. 16-20):

VPQALEPLPIVYYVGRKPKVEQLSN,
VSQDLEPLTILYYIGKTPKIEQLSN,
VPQDLEPLTILYYVGRTPKVEQLSN,
VPQTLDPLPIIYYVGRNVRVEQLSN,
and
VPDVLEPLPIIYYVGRTAKVEQLSN;

as well as homologs and analogs thereof; wherein
A=Ala=Alanine
R=Arg=Arginine
N=Asn=Asparagine
D=Asp=Aspartic acid
B=Asx=Asparagine or aspartic acid
C=Cys=Cysteine
Q=Gln=Glutamine
E=Glu=Glutamic acid
Z=Glx=Glutamine or glutamic acid
G=Gly=Glycine
H=His=Histidine
I=Ile=Isoleucine
L=Leu=Leucine
K=Lys=Lysine
M=Met=Methionine
F=Phe=Phenylalanine
P=Pro=Proline
S=Ser=Serine
T=Thr=Threonine
W=Trp=Tryptophan
Y=Tyr=Tyrosine
V=Val=Valine It is apparent from an inspection of the amino acid sequences of the peptides listed above that certain amino acid substitutions in the sequences are allowable without abolishing the chemotactic properties of the peptides in order to provide some guidance to the skilled practitioner in preparing analogs. For example, in the seven amino acid (7 mer) peptide 368-374, the two tyrosines, which are the second and third N-terminal residues, and the glycine, which is the fifth residue in the sequence, are invariant, i.e., they are present in all of the peptides (including the larger peptides of groups (B)-(D). The first and forth positions in the sequence appear to require a hydrophobic amino acid. Thus, 7 mer peptide analogs could contain Ala, Gly, Val, Leu or Ile at position one and/or four. Likewise, position six appears to require a basic amino acid. Thus an Arg, Lys or His may be present at this position. Position five appears to allow more variation in amino acid sequence. Preparation of such peptide analogs and determination of their chemotactic properties is considered relatively straightforward for one of skill in the art. Similar considerations may be taken into account for preparing analogs of the longer peptides of groups (B)-(D) above.

The peptides of the invention induce chemotaxis of fibroblasts and inflammatory cells (neutrophils and monocytes/macro-phages) in in vitro assays. Assays for measuring chemotaxis induced by the peptides can utilize either fibroblasts or monocytes. The following sets forth a representative assay for measuring fibroblast chemotaxis induced by the peptides of the invention:

Target cells used in in vitro chemotaxis assays were infant foreskin fibroblasts obtained by establishing monolayer cultures from explants of tissue. Cells were maintained in Eagle's minimum essential medium (MEM) supplemented with non-essential amino acids, antibiotics, 50 ug/ml ascorbic acid, and 9% fetal calf serum (FCS). Cells were passaged by trypsinization every 3–5 days.

Infant foreskin fibroblasts were harvested from monolayer culture by gentle trypsinization, washed twice in serum-free Eagles's MEM and adjusted to a final concentration of 250,000 cells/mi. The cell suspension (0.4 ml) was added to the upper compartments of blind well modified Boyden chemotaxis chambers. The peptides of the invention being assayed for chemotactic activity were solubilized in glycylglycine (0.015M) buffered NaCl (0.14M), pH 7.2, hereinafter referred to as GGBS, and diluted 50% with serum-free MEM. Test substances were added to the lower compartment of the chemotaxis chambers. Gelatin-treated polycarbonate filters (8 micron pore size) were interposed between the lowest compartment and the upper cell compartment. Loaded chambers were incubated at 37° C. in a humidified atmosphere containing 5% $CO_2$ for 150 minutes. After incubation, the chambers were disassembled, the filters removed, stained with hematoxylin, and mounted on glass cover slips. Fibroblast chemotaxis was quantitated by counting the number of fibroblasts in 20 oil immersion fields (OIF) that migrated and adhered to the lower surface of each filter. Samples were tested in quadruplicate and results are expressed as mean number of fibroblasts per 20 OIF ± standard error of the mean (SEM). Chemotaxis neutralization studies were performed by adding TGF-$\beta$1 or fibronectin to the upper cell compartment and testing for effects on fibroblast migration to the TGF-$\beta$ peptides.

Human peripheral blood neutrophils and monocytes, isolated from whole blood using standard techniques may also be used in the chemotaxis assays, in a manner similar to infant foreskin fibroblasts, to measure the chemotactic activity of the peptides towards inflammatory cells. Such cells may also be maintained in supplemented MEM as above, to which 5–10% FCS may be added. When using neutrophils and monocytes, instead of fibroblasts, the polycarbonate filters used in the modified Boyden chambers had pore sizes of 2 and 3 microns, respectively. As above, all assays were carried out in quadruplicate.

The peptides of the invention were also found to induce fibroblast proliferation in vitro. Fibroblast proliferation was measured in low-passaged (fewer than 8) fibroblast cultures. Fibroblasts were added at low density (20,000 cells/well) to Falcon 3047 multiwell plates in maintenance medium. After incubation at 37° C. in a humidified atmosphere containing 5% $CO_2$ for 16 h, the medium was removed from each well and replaced with 450 $\mu$l serum-free maintenance medium containing 0.1% BSA and 50 $\mu$l aliquots of sterilized test sample. Each sample being tested for mitogenic activity was added to triplicate wells. Since preliminary studies indicated maximal [$^3$H]TdR incorporation occurred in fibroblasts exposed to the peptides of the invention at 96 h, all cultures were incubated for 72 h, at which time each, well was pulsed with [$^3$H]TdR (1.0 uCi, sp. act. 1.9 ci/mmole, New England Nuclear, Boston, MA). After 24 h additional incubation, the medium was removed from each well. The fibroblast monolayers were washed × 3 with warm PBS. The PBS was removed from each well and replaced with 500 $\mu$l % SDS. After 15 min. of repeated agitation of each multi-well plate, a 250 $\mu$l aliquot from each well was transferred to scintillation vials containing Bio-Safe II (Research Products International Corp., Mt. Prospect, IL), cooled for 4 h, and counted in a scintillation counter. Fibroblast proliferation was expressed as "Mean CPM ± SEM" per well of the replicates. The standard errors were less than 15% of the mean values by this assay.

The peptides of the invention were also found to stimulate collagen production by fibroblasts. Collagen production by fibroblasts in response to the peptides of the present invention was measured utilizing a modified Peterofsky-Diegelman assay. The assay is used to determine whether the peptides of the invention stimulate or inhibit collagen production by fibroblasts.

Low passage (4–12 subpassages) infant foreskin fibroblasts were plated out at a density of $10^5$ cells/well in Falcon 3008 multiwell plates in complete maintenance medium containing 10% FCS. After cells reached confluency (72 hr), the medium was changed daily for 3 days, each time being replaced with serum-free maintenance medium containing fresh ascorbic acid. Samples (50$\mu$l) were added to triplicate wells containing 450 $\mu$l serum-free MEM supplemented with fresh ascorbic acid and [$^3$H]-proline (sp. act. 20 Ci/mmole), but no non-essential amino acids. After an additional 24 hr of culture, supernatants were reacted with protease-free bacterial collagenase to digest all collagen. Similar aliquots of unreacted supernatants and bacterial collagenase-treated supernatants were precipitated with cold 10% trichloroacetic acid (TCA) and were centrifuged for 5 minutes in a Beckman microfuge. Aliquots of the supernatants, after TCA precipitated proteins were pelleted, were placed in vials containing Hydrofluor and then were counted in a scintillation counter. CPM from TCA precipitated supernatants not reacted with bacterial collagenase were subtracted from each culture. The resulting CPM was a reflection of the collagen produced by that culture.

The ability of the peptides to competitively bind to fibroblasts and monocytes (compared with purified TGF-$\beta$1) were also carried out in order to determine whether the peptides of the invention bound to cellular receptors for TGF-$\beta$. TGF-$\beta$1 reparations for use in competitive binding assays were highly purified (>95% purity) natural porcine platelet-derived TGF-$\beta$1, human recombinant ("hr") TGF-$\beta$1 (R & D Systems, Minneapolis, MN) and [$^{125}$I]-hrTGF-$\beta$1 (sp. act. 3950 C:/mmole, New England Nuclear, Boston, Mass.).

Competitive binding studies employing fibroblasts were performed on monolayers of nearly confluent fibroblasts grown in 24-well tissue culture plates (Falcon Plastics, Oxnard, CA). Binding medium (RPMI 1640, 20mM HEPES, 0.1 sodium azide, pH 7.4 with 0.1% fatty acid free BSA) (250 $\mu$l) was then added to wells containing fibroblast monolayers with or without various concentrations of TGF-$\beta$1 peptides and [$^{125}$I]-hrTGF-$\beta$1 (0.05 nM, sp. act. 3950 Ci/mmole). To determine nonspecific binding, a 500 fold molar excess (10 nM) of unlabeled hrTGF-$\beta$1 was added to certain wells. After 2h incubation at 4° C., medium was removed from each well (for determination of unbound counts), and the fibroblast monolayers were washed × 2 with ice cold PBS containing 0.1% fatty acid free BSA (500 $\mu$l each wash). Cell layers were solubilized with PBS containing 1% SDS (100 $\mu$l), transferred to tubes, and counted in a gamma counter.

The human monocytic leukemia cell line, THP-1 (American Type Culture Collection, Rockville, Md.), was maintained in suspension cultures in RPMI 1640 supplemented with penicillin (100 units/$\mu$l), streptomycin (100 $\mu$g/$\mu$l), and amphoteracin B (1 $\mu$g/$\mu$l). For competitive binding studies, the THP-1 cells were incubated (2.5×10⁶ cells) in 88 μl binding medium for 2h at 4° C. in the absence and presence of different concentrations of the peptides according to the invention and [$^{125}$I]-hrTGF-$\beta$1 (0.05 nM, sp. act. 3950 Ci/mmole). Nonspecific binding was assessed by pretreating additional cells with 10 nM unlabeled hrTGF-$\beta$1. Cells with bound [$^{125}$I]-hrTGF-$\beta$1 were removed by centrifugation through a mixture of phthalate oils. Free and bound counts were determined in a gamma counter.

For both THP-1 and fibroblast binding assays, bound counts of [$^{125}$I]-hrTGF-$\beta$1 were corrected for nonspecific binding by subtracting from each value the cell bound counts obtained with 500 fold molar excess of unlabeled TGF-$\beta$1. For each assay, the bound counts corrected for nonspecific binding obtained with [$^{125}$I]-hrTGF-$\beta$1 in the absence of added peptides was considered to be 100%. The binding of [$^{125}$I]-hrTGF-$\beta$1 in the presence of each peptide was expressed as a percentage of the degree of binding of [$^{125}$I]-hrTGF-$\beta$1 to cells with no added peptides derived by the following formula:

$$\text{Bound \% of TGF-}\beta 1 = \frac{\text{cpm bound with peptide}}{\text{ycm bound without peptide}} \times 100$$

All samples were tested in triplicate, and the standard error of cell bound cpm for each of the replicates was less than 15% of the mean value for each sample.

The ability of the peptides to induce cellular chemotaxis and a fibrogenic response (fibroblast proliferation and collagen synthesis) in vivo may be measured by intradermal injection of the peptides into the skin of guinea pigs. Generally, the in vivo, guinea pig skin studies were carried out according to the following protocol:

8 mg/cc stocks of the peptides according to the present invention in Dulbecco's PBS were sterile filtered using a 0.45μ syringe filter. PBS plus ZYDERM ™ collagen (Collagen Corp., Inc.) was used as a control. Peptide stocks were diluted 1:1 with ZYDERM ™ collagen (35 mg/ml), resulting in a 4 mg/ml peptide-collagen suspension. Peptide-collagen suspensions were kept on ice at all times and drawn up in 1 cc syringes fitted with 27 or 28 gauge needles.

Guinea pigs (Hartley strain, female, weanlings) were shaved on the left and right sides of their abdomens. 100 μl of a suspension of peptide-collagen was injected intradermally in one site on each side of each guinea pig. Each site was circled with an indelible ink pen. Pigs were remarked after 3 days. At appropriate times after injection, guinea pigs were sacrificed via CO$_2$ narcosis. Animals were shaved and a depilatory was used to remove remaining stubble. Injection sites were excised using a skin biopsy punch (6mm). Tissue was placed in vials with 10% neutral buffered formalin. Sections were processed for staining with H + E and Masson's Trichrome.

The ability of the peptides of the present invention to promote wound healing may be monitored according to standard procedures, e.g. as disclosed in U.S. Pat. No. 5,104,977, which in turn is based on the protocol disclosed in T. K. Hunt et al., Amer. J. Surgery 114:302, 1967. This protocol utilizes empty Schilling-Hung wire mesh wound chambers surgically implanted subcutaneously into the backs of rats who respond to these chambers as if they were wounds. Eventually the implanted chambers become filled with fibroblasts and collagen. Several days after the chambers are inserted, the chambers become encapsulated with connective tissue, but there are few cells within the chambers. There is thus a defined enclosed space within the chambers to quantitate a wound healing response.

At this time, daily injections of the peptides of the invention, either alone, admixed with collagen or covalently attached to a carrier protein, e.g. serum albumin via a disulfide linkage (approximately 0.1 mg samples prepared in sterile PBS) may be administered. Following administration of the various peptide samples for several days, the rats are sacrificed and the chambers removed. Following excision of all connective tissue from the outside of the wire mesh chambers, the content of chambers may be examined for presence and proliferation of fibroblasts and any increase in collagen production. The measurements utilize assays as described above, as well as histological examination to confirm the occurrence of fibroblast proliferation and collagen formationin the chambers.

In view of the above noted properties of the peptides of the invention, it is contemplated that the present peptides may be used in promoting wound healing. Another aspect of the invention is directed to methods for promoting wound healing by administering the peptides of the present invention to a patient for a time and under conditions to promote wound healing.

The peptides of the present invention may be administered to a host as a pharmaceutical composition in a therapeutically effective amount. The pharmaceutical compositions contain a therapeutically effective dosage of at least one of the peptides according to the present invention, together with a pharmaceutically acceptable carrier.

Preferably, compositions containing the peptides of the invention are applied topically for the promotion of surface wound healing. There are no limitations as to the type of wound or other surface trauma that can be treated, and these include (but are not limited to): first, second and third degree burns (especially second and third degree); surgical incisions, including those of cosmetic surgery; wounds, including lacerations, incisions, and penetrations; and surface ulcers including decubital (bed-sores), diabetic, dental, hemophiliac and varicose. Although the primary concern is the healing of major wounds by inducing chemotaxis and proliferation fibroblasts and inflammatory cells, it is contemplated that the compositions may also be useful for minor wounds, and for cosmetic regeneration. It is also contemplated that the peptide compositions may be utilized by the topical application to internal surgical incisions.

When applied topically, the peptide compositions may be combined with other ingredients, such as carriers and/or adjuvants. The peptides may also be covalently attached to a protein carrier, such as albumin, so as to minimize diffusion of the peptides. There are no limitations on the nature of such other ingredients, except that they must be pharmaceutically acceptable, efficacious for their intended administration and cannot degrade the activity of the active ingredients of the compositions. When the peptide compositions of this invention are applied to burns, they may be in the form of an irritant, preferably in combination with physiological saline solution. The peptide compositions can also be in the form of ointments or suspensions, preferably in combination with purified collagen. The peptide compositions also may be impregnated into transdermal patches, plasters and bandages, preferably in a liquid or semi-liquid form.

The peptides of the invention may also be systematically administered for promoting the healing of internal wounds and similar trauma. Since the peptides of the invention do not appear to possess the tumorigenic properties of intact TGF-βs (i.e., they do not cause anchorage-independent growth of cells in soft agar), systemic application should not be limited.

When applied systemically, the peptide compositions may be formulated as liquids, pills, tablets, lozenges or the like, for enteral administration, or in liquid form for parenteral injection. The peptides (or peptide-protein conjugates) may be combined with other ingredients such as carriers and/or adjuvants. There are no limitations on the nature of such other ingredients, except that they must be pharmaceutically acceptable, efficacious for their intended administration and cannot degrade the activity of the active ingredients of the compositions.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dosage of the peptide may also contain an inert diluent, an assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dosage.

The precise therapeutically effective amount of peptides to be used in the methods of this invention to promote wound healing cannot be stated because of the nature of the activity of TGFs and the nature of healing wounds and/or other trauma. It must also be obvious that the amount of a chemotactic and/or cell growth promoting substance (such as the peptides of this invention) that must be utilized will vary with the size of the wound or other trauma to be treated.

Since the peptide compositions of this invention both provoke and sustain cellular migration, proliferation and regeneration, a continual application or periodic reapplication of the compositions is indicated and preferred.

The amount of peptide of the invention per unit volume of combined medication for administration is also very difficult to specify, because it depends upon the amount of active ingredients that are afforded directly to the regenerating cells of the wound or other trauma situs. However, it can generally be stated that the peptides should preferably be present in an amount of at least about 1.0 nanogram per milliliter of combined composition, more preferably in an amount up to about 1.0 milligram per milliliter.

Systemic dosages depend on the age, weight and conditions of the patient and on the administration route. For example, a suitable dosage for the administration to adult humans ranges from about 0.01 to about 100 mg per kilogram body weight. The preferred dosage ranges from about 0.5 to about 5.0 mg per kilogram body weight.

As used herein, a pharmaceutically acceptable carrier includes any and all solvents, dispersion media, coatings, antibacterial and antifungal agents, isotonic agents and the like. The use of such media and agents are well-known in the art.

The following examples further illustrate the invention.

EXAMPLE 1

The peptides listed in Table I, which correspond to the designated sequences in TGF-β1 were synthesized and tested for their ability to induce chemotaxis of fibroblasts, monocytes and neutrophils. As shown in FIG. 1, fibroblasts, monocytes and neutrophils migrated in a dose dependent fashion to peptide 340-391, but not to peptide 280-339, which corresponds to the amino terminal portion of TGF-β1 monomer. The peptides were added to the lower chambers of modified Boyden chambers. The results are expressed as number of cells per 20 oil immersion fields ("OIF").

TABLE I*

| HUMAN TGF-β1 PEPTIDES SYNTHESIZED | |
|---|---|
| Residue Number | Amino Acid Sequence |
| 280–339 | Ala Leu Asp Thr Asn Tyr Cys Phe Ser Ser Thr Glu Lys Asn Cys Cys Val Arg Gln Leu Tyr Ile Asp Phe Arg Lys Asp Leu Gly Trp Lys Trp Ile His Glu Pro Lys Gly Tyr His Ala Asn Phe Cys Leu Gly Pro Cys Pro Tyr Ile Trp Ser Leu Asp Thr Gln Tyr Ser Lys |
| 340–391 | Val Leu Ala Leu Tyr Asn Gln His Asn Pro Gly Ala Ser Ala Ala Pro Cys Cys Val Pro Gln Ala Leu Glu Pro Leu Pro Ile Val Tyr Tyr Val Gly Arg Lys Pro Lys Val Glu Gln Leu Ser Asn Met Ile Val Arg Ser Cys Lys Cys Ser |
| 280–293 | Ala Leu Asp Thr Asn Tyr Cys Phe Ser Ser Thr Glu Lys Asn |
| 296–322 | Val Arg Gln Leu Tyr Ile Asp Phe Arg Lys Asp Leu Gly Trp Lys Trp Ile His Glu Pro Lys Gly Tyr His Ala Asn Phe |
| 328–354 | Pro Tyr Ile Trp Ser Leu Asp Thr Gln Tyr Ser Lys Val Leu Ala Leu Tyr Asn Gln His Asn Pro Gly Ala Ser Ala Ala |
| 358–382 | Val Pro Gln Ala Leu Glu Pro Leu Pro Ile Val Tyr Tyr Val Gly Arg Lys Pro Lys Val Glu Gln Leu Ser Asn SEQ ID NO. 16 |
| 366–387 | Pro Ile Val Tyr Tyr Val Gly Arg Lys Pro Lys Val Glu Gln Leu Ser Asn Met Ile Val Arg Ser SEQ ID NO. 11 |
| 364–378 | Pro Leu Pro Ile Val Tyr Tyr Val Gly Arg Lys Pro Lys Val Glu SEQ ID NO. 6 |
| 368–374 | Val Tyr Tyr Val Gly Arg Lys SEQ ID NO. 1 |

*Peptides listed were patterned from the published sequence of human TGF-β1. The peptides were synthesized by the solid-phase technique of Merrifield, purified by reverse phase HPLC, and the amino acid compositions and sequences confirmed as described in Materials and Methods. The numbering of the peptide residues is as per Derynck et al.

EXAMPLE 2

Peptides 280–293, 296–322, 328–354, 358–382 (SEQ ID NO. 16), 366–387 (SEQ ID NO. 11), 364–378 (SEQ ID NO. 6) and 368–374 (SEQ ID NO. 1) of Table I, whose sequences correspond to the designated regions of TGF-$\beta$1 were tested in chemotaxis assays for the ability to induce migration of fibroblasts, monocytes and. neutrophils. The peptides were added to the lower compartments of modified Boyden chambers at the indicated concentration.

Because the peptides were tested in different experiments, migration was expressed as "Migration Index" which is obtained by dividing the number of cells migrating in response to medium into the number of cells migrating in response to each peptide. A positive chemotactic control, peptide 340–391 gave migration indices between 7–11.

As shown in FIG. 2, the results of the assays indicated that none of the peptides derived from the N-terminal half of TGF-$\beta$1 (peptides 280–293, 296–322 and 328–354) were able to induce migration of any of the tested cell types.

FIG. 3 demonstrates that the peptides (358–382 (SEQ ID NO. 16), 366–387 (SEQ ID NO. 11), 364–378 (SEQ ID NO. 6) and 368–374 (SEQ ID NO. 1)), contain the 7-mer peptide spanning residues 368–374,i.e., Val Tyr Tyr Val Gly Arg Lys, induced migration of fibroblasts, monocytes and neutrophils in a dose dependent fashion. The THP-1 human monocytic leukemia cell line chemotactically responded to the 7-mer containing. peptides in a similar fashion.

EXAMPLE 3

Zigmond-Hirsch checkerboard analysis (Zigmond & Hirsch, J. Exptl. Med. 137:387, 1972) was performed to determine whether the 7-mer peptide 368–374 (Val Tyr Tyr Val Gly Arg Lys) induced chemotaxis of fibroblasts, monocytes and neutrophils. As shown in Table II, peptide 368–374 (SEQ ID NO.1) induced primarily chemotaxis of fibroblasts, since it caused cell migration in the lower (test) compartment in excess of the amount present in the upper (cell) compartment of the modified Boyden chambers. Similar results were obtained with monocytes and neutrophils.

TABLE II

Zigmond-Hirsch Checkerboard Analysis of Peptide 368–374 (SEQ ID NO. 1)-Induced Fibroblast Migration*

| Upper Compartment Peptide 368–374 [M] | Lower Compartment Peptide 368–374 [M] | | | |
|---|---|---|---|---|
| | $7.0 \times 10^{-6}$ | $1.4 \times 10^{-6}$ | $7.0 \times 10^{-7}$ | 0 |
| | Fibroblasts per 20 OIF (mean ± SEM) | | | |
| $7.0 \times 10^{-6}$M | 11 ± 1 | 8 ± 1 | 7 ± 1 | 7 ± 1 |
| $1.4 \times 10^{-6}$M | 24 ± 2 | 9 ± 1 | 10 ± 1 | 9 ± 1 |
| $7.0 \times 10^{-7}$M | 39 ± 4 | 24 ± 2 | 10 ± 1 | 8 ± 1 |
| 0 | 58 ± 5 | 38 ± 2 | 20 ± 3 | 9 ± 1 |

*TGF-$\beta$1 peptide 368–374 was added at the concentrations indicated to the upper and/or lower compartments of modified blindwell Boyden chambers in quadruplicate, and migration of fibroblasts was quantitated.

EXAMPLE 4

Figure 4:
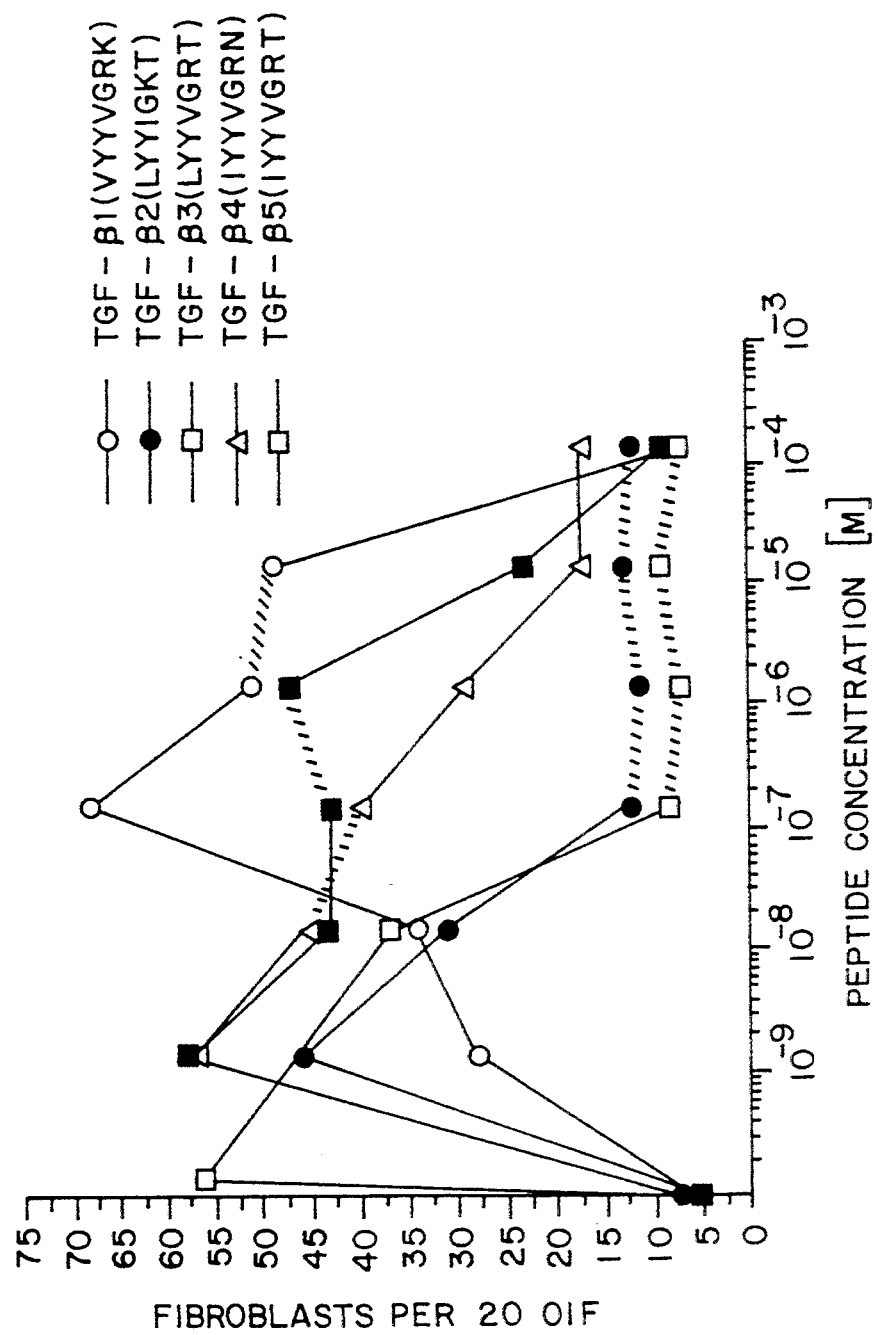
FIG. 4 is a graph showing the chemotactic response of fibroblasts to 7-mer peptides 368–374 (SEQ ID NO. 1–5).

The following 7-mer peptides (peptides 368–374, corresponding to amino acids 368–374 of TGF-$\beta$1): VYYVGRKK (SEQ ID NO. 1), LYYIGKT (SEQ ID NO. 2), LYYVGRT (SEQ ID NO. 3), IYYVGRN (SEQ ID NO. 4) and IYYVGRT (SEQ ID NO. 5), were synthesized by the Merrifield technique, purified by HPLC and tested at different concentration in the same assay for their ability to stimulate chemotaxis of human infant foreskin fibroblasts in vitro in modified Boyden chambers as described above. As shown in FIG. 4, all peptides induced fibroblast chemotaxis at all of the concentration tested. These studies suggest that this homologous region of all five TGF-$\beta$ isoforms is crucial for inducing fibroblast chemotaxis.

EXAMPLE 5

Figure 5:
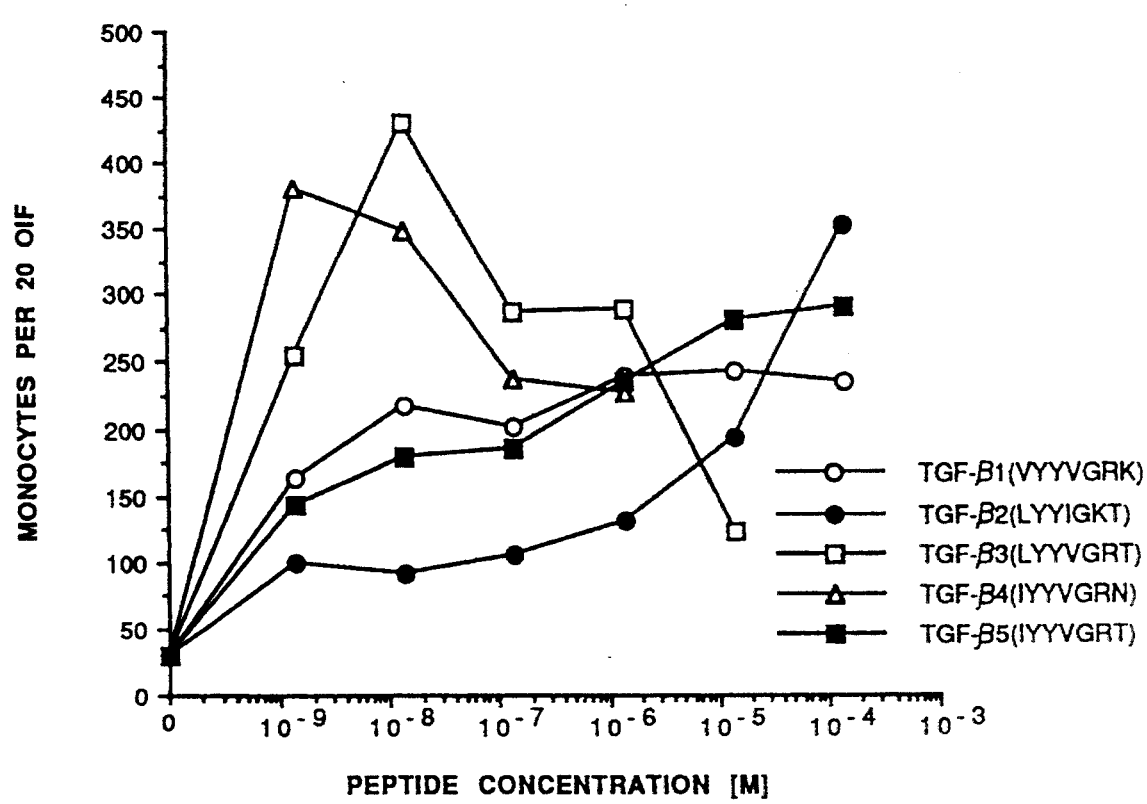
FIG. 5 is a graph showing the chemotactic response of monocytes to 7-mer peptides 368–374 (SEQ ID NO. 1–5).

The following 7-mer peptides (peptides 368–374, corresponding to amino acids 368-374 of human TGF-$\beta$1): VYYVGRK (SEQ ID NO. 1), LYYIGKT (SEQ ID NO. 2), LYYVGRT (SEQ ID NO. 3), IYYVGRN (SEQ ID NO. 4) and IYYVGRT (SEQ ID NO. 5) were synthesized by the Merrifield technique, purified by HPLC, and tested at different concentrations in the same assay for their ability to stimulate chemotaxis of human peripheral blood monocytes in vitro modified Boyden chambers. As shown in FIG. 5, all five 7-mer peptides induced monocyte chemotaxis at all of the concentrations tested. These studies suggest that this homologous region of all five TGF-$\beta$ isoform is crucial for inducing monocyte chemotaxis.

EXAMPLE 6

Fibroblast proliferation experiments in response to the 7-mer peptides (peptides 368–374) were carried out as generally described above. Cultures of subconfluent infant foreskin fibroblasts were grown in serum-free Eagle's minimum essential media with and without various concentrations of the following 7-mer peptides: VYYVGRK (SEQ ID NO. 1), LYYIGRT (SEQ ID NO. 2), LYYVGRT (SEQ ID NO. 3), IYYVGRN (SEQ ID NO. 4) and IYYVGRT (SEQ ID NO.5). Human recombinant TGF-$\beta$1 (25 ng/ml) was used as a positive control. The cultures were pulsed with [$^3$H]thymidine after 72h of culture, and the fibroblast monolayers were harvested 24h later after extensive washing with phosphate buffered saline and solubilization in detergent. All cultures were performed in triplicate and results were expressed as the means of triplicate values as counts per minute (CPM) per well.

Figure 6:
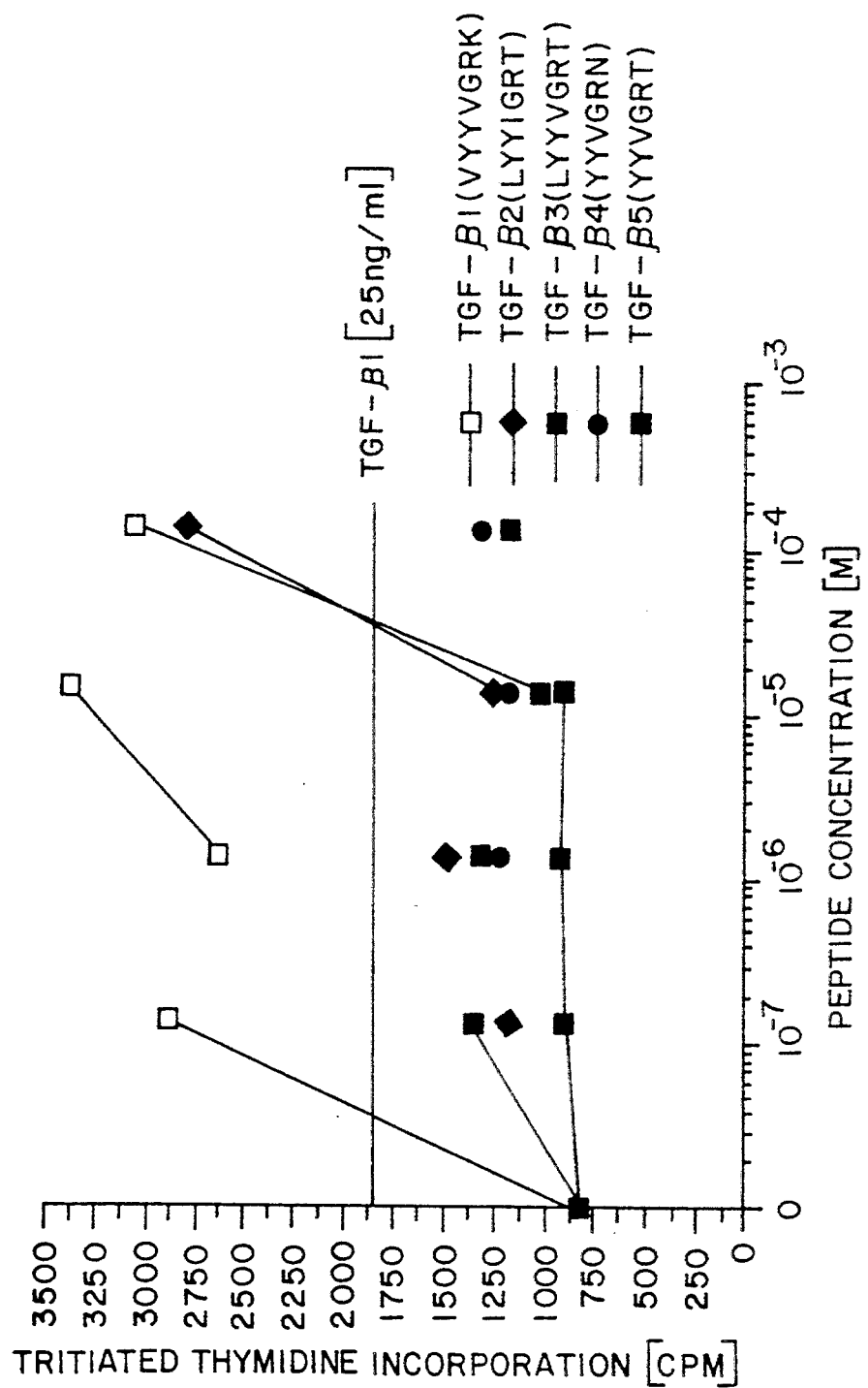
FIG. 6 is a graph showing fibroblast proliferation in response to 7-mer peptides 368–374 (SEQ ID NOs. 1–5).

As shown in FIG. 6, the VYYVGRK 7-mer peptide (SEQ ID NO. 1) was most effective in inducing fibroblast growth, exceeding that obtained with human recombinant TGF-$\beta$1. The other 7-mer peptides also stimulated fibroblast growth, but with less potency than VYYVGRK (SEQ ID NO. 1). These data show that the 7-mer peptide corresponding to each of the five TGF-$\beta$ is crucial for inducing fibroblast proliferation.

EXAMPLE 7

Figure 7:
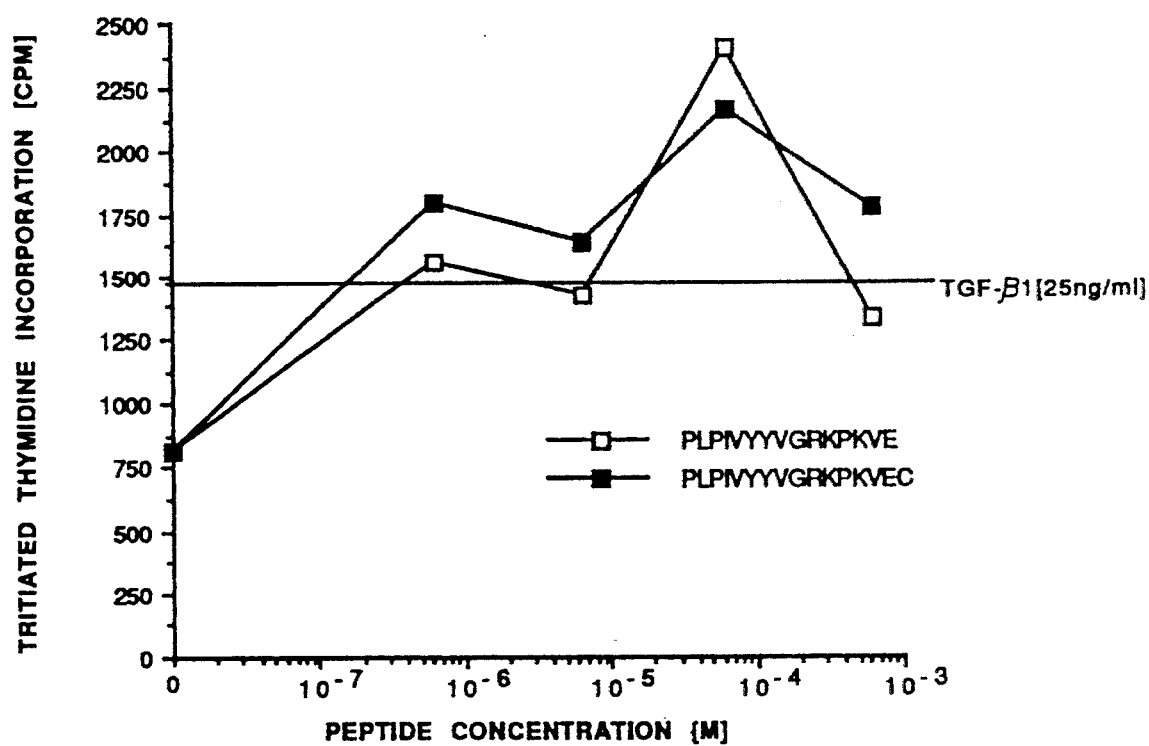
FIG. 7 is a graph showing fibroblast proliferation in response to the 15-mer peptide 364–378 (SEQ ID NO. 6) and an analog of the 15-mer peptide 364–368 (SEQ ID NO. 6) containing a C-terminal Cys.

FIG. 7 depicts the result of a fibroblast proliferation assay measured in response to an analog of the 15-mer peptide 364–378, PLPIVYYGRKPKVE (SEQ ID NO. 6), which contained an additional C-terminal cysteine, through which the peptide could be covalently attached to a carrier protein, such as serum albumin.

Subconfluent human infant foreskin fibroblasts were cultured in serum-free Eagle's minimum essential medium with and without different concentrations of the 15-mer peptide 364-378, PLPIVYYVGRKPKVE (SEQ ID NO. 6) and the 15-mer peptide (SEQ ID NO. 6) containing a C-terminal cysteine (i.e., PLPI-VYYVGRKPKVEC). All samples were tested in triplicate. After 72 h, culture wells were pulsed with

[³H]thymidine and 24 h later, after extensive washing, the cells labeled with [³H]thymidine were solubilized with detergent and radioactivity was quantitated in a scintillation counter. Results were expressed as mean counts per minute (CPM) per well. A control consisted of human recombinant TGF-$\beta$1 (25 ng/ml).

These data show that attaching a C-terminal cysteine to the peptide does not alter its ability to stimulate proliferation of fibroblasts in vitro.

EXAMPLE 8

This example provides a protocol by which peptide analogs according to the present invention containing a C-terminal cysteine may be attached to a carrier protein.

The peptides of the invention are synthesized by the Merrifield technique to contain a COOH terminal cysteine for ease of coupling to the aluminum carrier. The synthetic peptide is coupled through the sulhydryl group to human serum albumin that has been activated with m-maleimidobenzoyl-N-hydroxysuccinimide ester. Specifically, 4 mg of human serum albumin in 0.43 ml of 10 mM sodium phosphate buffer, pH 7.2 is reacted with 0.7 mg of m-maleimidobenzoyl-N-hydroxysuccinimide ester in dimethylformamide and stirred at room temperature for 30 min. The reaction products are then passed through a Sephadex G-25 column equilibrated with 50 mM sodium phosphate buffer, pH 6.0. This removes free m-maleimidobenzoyl-N-hydroxysuccinimide ester. The activated albumin that elutes the serum exclusion volume is mixed with 2 mg of the peptide in 0.2 ml of 0.1M sodium borate buffer (pH 9.0). After adjusting the pH to 7-7.5, the reaction is allowed to continue for 3 h with stirring at room temperature. The coupled peptide albumin complex is then dialyzed free of salt, then lyophilized and used.

EXAMPLE 9

Figure 8:
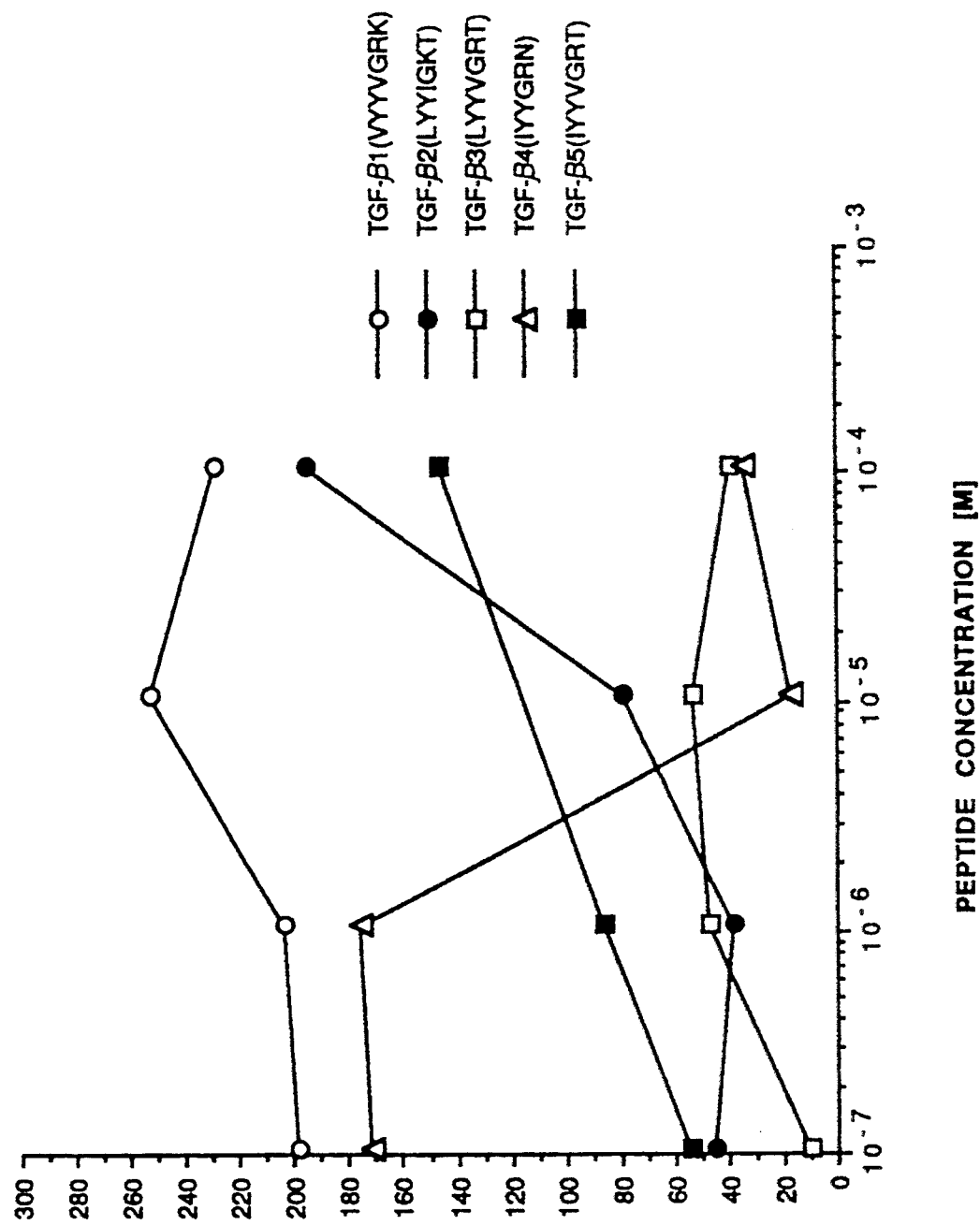
FIG. 8 is a graph showing collagen production by fibroblasts in response to 7-mer peptides 368–374 (SEQ ID NOs. 1–5).

Collagen production was measured following administration of the various 7-mer peptides peptides 368-374 (SEQ ID NOs. 1-5) to fibroblasts. Peptides VYYVGRKK (SEQ ID NO. 1), LYYIGKT (SEQ ID NO. 2), LYYVGRT (SEQ ID NO. 3), IYYVGRN (SEQ ID NO. 4) and IYYVGRT (SEQ ID NO. 5) were synthesized by the Merrifield technique, purified by HPLC, and tested at different concentrations in the same assay for their ability to stimulate production of collagen in confluent cultures of infant foreskin fibroblasts. Collagen production was measured by incorporation of [³H]proline into collagenase-sensitive protein. All samples were tested in triplicate, and values represent the mean of triplicate determinations. Data are expressed as "% stimulation" of collagen production relative to control production in cultures with plain culture medium only added. As shown in FIG. 8, all of the peptides stimulated collagen production to some degree, with peptide VYYVGRK (SEQ ID NO. 1) being the most potent. These studies suggest that this homologous region of all five TGF-$\beta$ species is crucial for inducing collagen production by fibroblasts.

EXAMPLE 10

Figure 9:
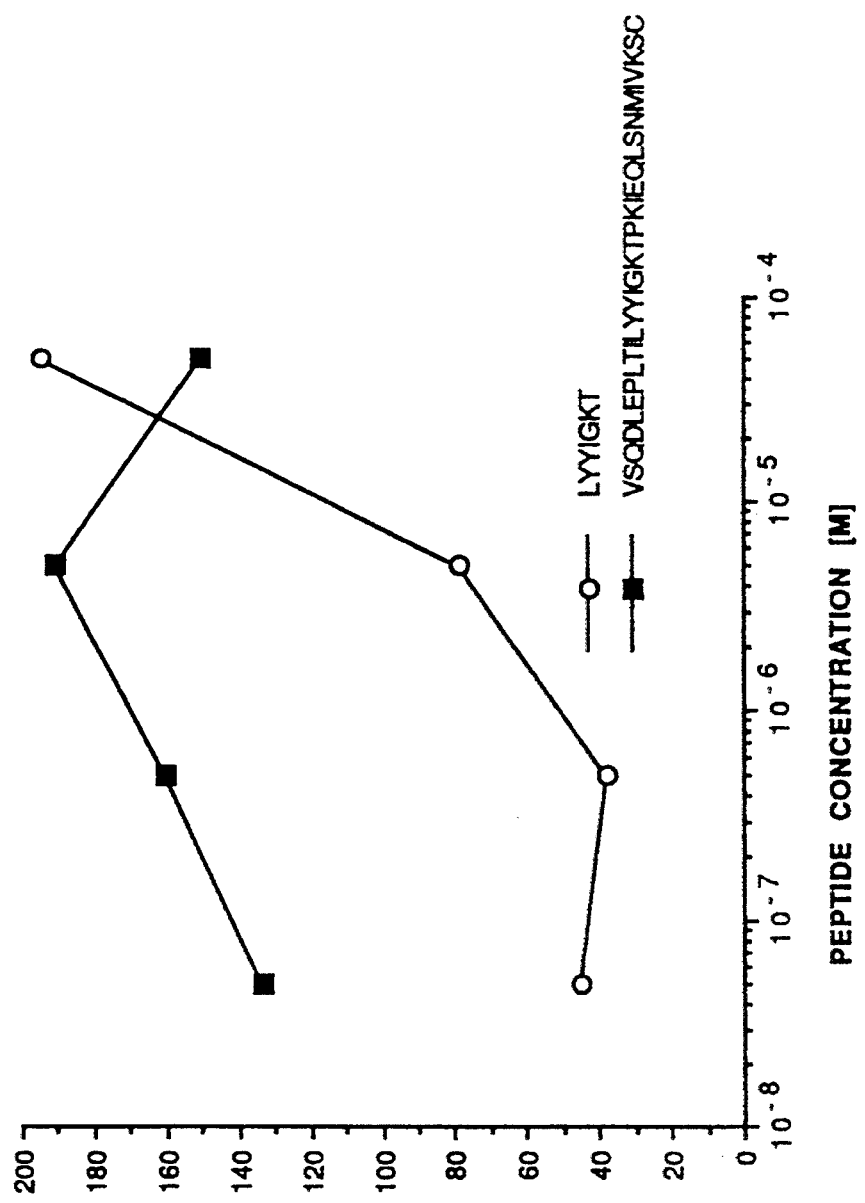
FIG. 9 is a graph showing collagen production by fibroblasts in response to the peptide having SEQ ID NO. 2 and a peptide analog of SEQ ID NO. 17.

Collagen production stimulated by peptides 368-374 having the sequence, LYYIGRT (SEQ ID NO. 2) and an analog of peptide 358-382 (SEQ ID NO. 17), containing six additional C-terminal amino acids, having the sequence VSQDLEPLTILYYIGKTPKIEQLSNMIVKSC, was measured. Human infant foreskin fibroblasts were cultured for 72 h with varying concentrations of peptide VSQDLEPLTILYYIGKTPKIEQLSNMIVKSC and peptide LYYIGRT (SEQ ID NO. 2). During the last 24 h of culture, [³H]proline was added to culture wells and after dialysis to remove free [³H]proline, collagenase-sensitive protein was determined. Values are expressed as "% stimulation of collagen production" relative to control cultures, which contained only medium. Samples were tested in triplicate, and means values of triplicate determination are shown. As shown in FIG. 9, both peptides stimulated collagen production, showing that peptide 368-374 LYYIGRT (SEQ ID NO. 2), is a critical sequence for stimulation of collagen production.

EXAMPLE 11

Figure 10:
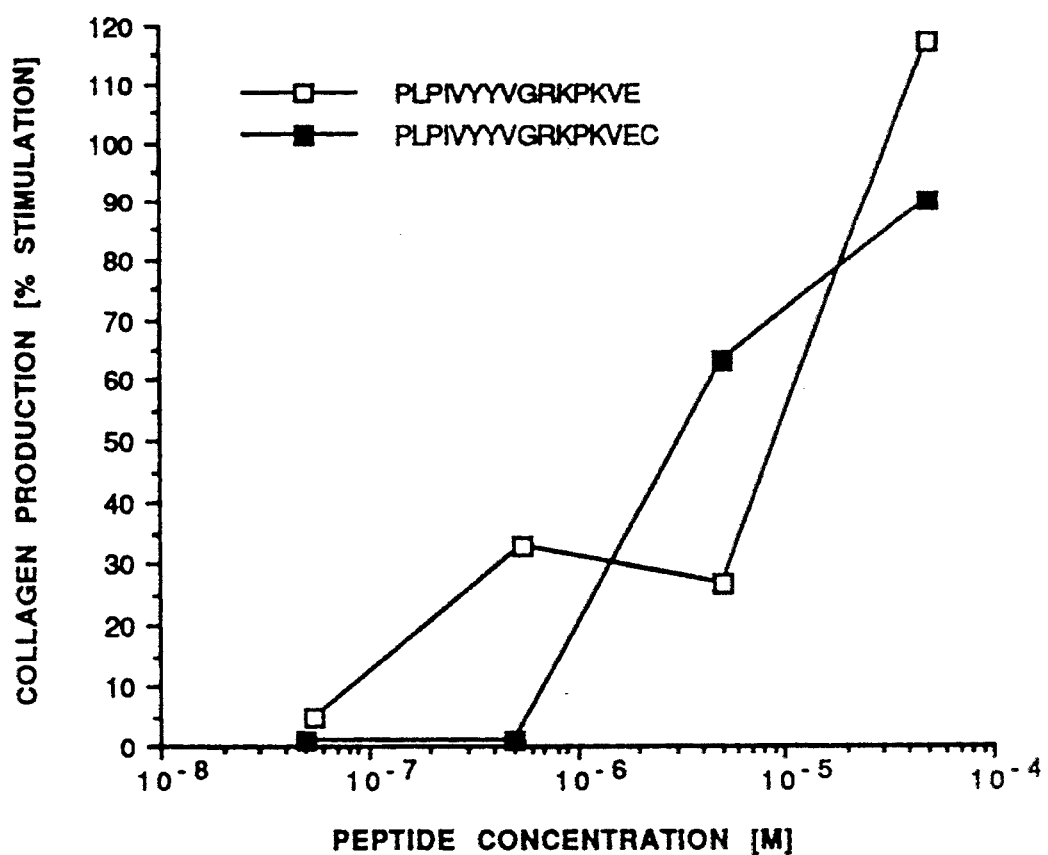
FIG. 10 is a graph showing collagen production by fibroblasts in response to 15-mer peptide 364–378 (SEQ ID NO. 6) and an analog of the 15-mer peptide containing a C-terminal Cys.

Collagen production induced by an analog of peptide 364-378 (SEQ ID NO. 6), containing a C-terminal cysteine was measured. Confluent human infant foreskin fibroblasts were cultured in serum-free Eagle's minimum essential medium with and without different concentrations of the 15-mer peptide 364-378 PLPIVYYVGRKPKVE (SEQ ID NO. 6) and peptide 364-378-cysteine having the sequence PLPIVYYVGRKPKVEC. All samples were tested in triplicate. After 48 h, culture wells were pulsed with [³H]proline. 24 h later, samples were dialyzed extensively and collagenase-sensitive protein was quantitated. Radioactivity was quantitated in a scintillation counter. Results are expressed as mean percent stimulation of collagen produced relative to unstimulated control cultures. As shown in FIG. 10, these data show that attaching a C-terminal cysteine to the 15-mer peptide does not alter its ability to stimulate collagen synthesis in fibroblasts in vitro.

EXAMPLE 12

Deactivation studies were utilized to determine whether the peptides of the invention containing the 7-mer peptide amino acid sequence induced chemotaxis via cellular receptors and mechanisms utilized by intact TGF-$\beta$. Previous studies demonstrated that cells can be "deactivated" to chemotax to a specific chemoattractant by preincubation with the chemoattractant (see, e.g., Postlewaite et al., J. Exptl. Med. 165:251, 1987).

Table III provides the results of deactivation experiments. The addition of TGF-$\beta$1 to fibroblasts or monocytes in the upper cell compartment of modified Boyden chambers resulted in a loss of the ability of these cells to migrate in a specific manner to peptides containing the 7-mer sequence spanning residues 368-374 (SEQ ID NOs. 1 and 6). The deactivation was specific for TGF-$\beta$1, as fibronectin (an unrelated chemoattractant) had no effect.

TABLE III

| Deactivation of Fibroblasts and Monocytes to the Peptides of the Invention by TGF-$\beta$1[1] | | |
|---|---|---|
| | Added by Upper Compartment | |
| Contents of Lower Compartment | TGF-$\beta$1 (50 pg/ml) | Media |
| Experiment 1 | | |
| Media | Mean Fibroblasts per 20 OIF ± SEM | |
| TGF-$\beta$1 (50 pg/ml) | 21 ± 2 | 7 ± 1 |
| Peptide 368-374 (SEQ ID NO. 1) (1.4 × 10⁻⁵M) | 23 ± 1* | 75 ± 2 |
| Peptide 364-378 (SEQ ID NO. 6) | 37 + 5* | 122 ± 8 |

TABLE III-continued

| | Deactivation of Fibroblasts and Monocytes to the Peptides of the Invention by TGF-β1[1] | |
|---|---|---|
| | Added by Upper Compartment | |
| Contents of Lower Compartment | TGF-β1 (50 pg/ml) | Media |
| (6.7 × 10⁻⁷M) Fibronectin (20 μg/ml) | 71 ± 6 | 74 ± 2 |
| Experiment 2 | | |
| | Mean Monocytes per 20 OIF + SEM | |
| Media | 47 ± 3 | 46 ± 2 |
| Peptide 368-374 (SEQ ID NO. 1) | 50 ± 5* | 138 ± 8 |

[1]Fibroblasts or monocytes were placed in modified Boyden Chemotaxis Chambers with or without TGF-β1 (50 pg/ml) added to the upper cell compartment, and migration to the various agents in the lower (test) compartment was measured.
*Values significantly different (p < 0.001) from that obtained by not adding TGF-β1 to the upper cell compartment of chemotaxis chamber.

EXAMPLE 13

Competitive binding assays were carried out to determine whether any of the disclosed synthetic peptides could compete with [$^{125}$I]-hrTGF-β1 for binding to TGF-β cellular receptors. Binding studies were repeatedly (three time for each cell type) performed using infant foreskin fibroblasts in monolayer culture, and the human monocytic leukemia cell line THP-β1, in which the target cells were preincubated with different concentrations of each of the peptides and then with [$^{125}$I]-hrTGF-β1 to determine whether binding of TGF-β1 was affected by the concometent presence of TGF-β1 peptides. As shown in a representative experiment in FIG. 11, none of the listed peptides were able to competitively displace [$^{125}$I]-hrTGF-β1 from fibroblast monolayers. These same peptides were also unable to compete with [$^{125}$I]-hrTGF-β1 for binding to THP-1 cells.

EXAMPLE 14

Figure 12:
FIG. 12 is a photomicrograph of Mason-Trichome stained guinea pig skin following injection of peptide PLPIVYYVGRKPKVE (SEQ ID NO. 6), showing extensive collagen synthesis.
Figure 13:
FIG. 13 is a photomicrograph of Mason-Trichone stained guinea pig skin following injection of collagen and saline.

In vivo fibrosis assays were performed. Guinea pigs were injected intradermally with 400 μg of either peptide VYYVGRK (SEQ ID NO. 1) or peptide PLPI-VYYVGRKPKVE (SEQ ID NO. 6) in a 100 μl volume of saline containing type I bovine collagen carrier 1.7 mg (Zyderm, Celtrex Corp. Palo Alto, Calif.). As a control, at a distant site on the same guinea pig, the collagen carrier plus saline was injected intradermally as a control. Nine days later, the animals were sacrificed, and the skin sectioned through the injection sites was processed for histology using Mason-Trichrome to stain collagen fibers. The degree of fibrosis was assessed at 400 × magnification to determine degree of replacement of surrounding subcutaneous fat with newly synthesized collagen. FIG. 12 is a Mason-Trichrome, 400 × migration of 9 day post intradermal injection of guinea pig skin with 100 μl, 400 μg peptide PLPI-VYYVGRKPKVE (SEQ ID NO. 1) in collagen carrier (1.7 mg). There is marked (score of 4) replacement of fat cells with newly synthesized collagen in the subcutaneous fatty layer. Fibroblasts are noted scattered throughout what was once subcutaneous fatty layer. FIG. 13 is a Mason-Trichrome 400 × magnification of 9 days post intradermal injection of the same guinea pig as in FIG. 8 at a distant site with saline and collagen carrier as a control. Note minimal (score of 1) replacement of fat cells with newly synthesized collagen. Few fibroblasts are visible in the subcutaneous fatty layer.

The degree of fibrosis was graded on a scale of 0 to 4. Where 0 equals no collagen deposition with tightly packed fat cells of normal appearance with a normal 7–10 fat cell thick layer; 1 equals replacement of 10 to 25% of the fat cells with collagen; 2 equals replacement of 25 to 50% of fat cells with collagen; 3 equals replacement of 50 to 75% of fat cells with collagen; and 4 equals 75 to 100% of fat cells replaced with collagen. Table IV sets forth the results of these studies.

TABLE IV

HISTOLOGIC SCORING OF GUINEA PIG SKIN INJECTED WITH TGF-β PEPTIDES

| Peptide | Guinea Pig Number | Score Peptide | Score Saline |
|---|---|---|---|
| PLPIVYYVGRKPKVE (SEQ ID NO. 6) | 1 | 4 | 1 |
| | 2 | 3 | 0 |
| | 3 | 4 | 1 |
| | 4 | 4 | 1 |
| VYYVGRK (SEQ ID NO. 1) | 5 | 1 | 1 |
| | 6 | 1 | 1 |
| | 7 | 1 | 0 |
| | 8 | 1 | 0 |

Guinea pigs 1-4 were injected intradermally with 400 μg of peptide PLPI-VYYVGRKPKVE (SEQ ID NO. 6) in 1.7 mg type I collagen carrier in a volume of 100 μl. Guinea pigs 5-8 were injected intradermally with 400 μg peptide VYYVGRK (SEQ ID NO. 1) in 1.7 mg type I collagen carrier in a volume of 100 μl. As a control, 100 μl mg type I collagen with saline was injected on the opposite side of each animal. Histologic scoring was performed in a blinded manner and graded on VYYVGRK (SEQ ID NO. 1) did not induce fibrosis, apparently due to its small size which permitted rapid diffusion out of the collagen gel.

What is claimed is:

1. A chemotactic peptide having an amino acid sequence as set forth in SEQ ID NO. 1, or a homolog, or an analog thereof.

2. A chemotactic peptide wherein the amino acid sequence of the peptide is selected from the group consisting of SEQ ID NO. 1, SEQ. ID NO. 2, SEQ ID NO. 3, SEQ ID NO. 4, SEQ ID NO. 5 and analogs thereof.

3. A chemotactic peptide wherein the amino acid sequence of the peptide is selected from the group consisting of SEQ ID NO. 6, SEQ ID NO. 7, SEQ ID NO. 8, SEQ ID NO. 9, SEQ ID NO. 10 and analogs thereof.

4. A chemotactic peptide wherein the amino acid sequence of the peptide is selected from the group consisting of SEQ ID NO. 11, SEQ ID NO. 12, SEQ ID NO. 13, SEQ ID NO. 14, SEQ ID NO. 15 and analogs thereof.

5. A chemotactic peptide wherein the amino acid sequence of the peptide is selected from the group consisting of SEQ ID NO. 16, SEQ ID NO. 17, SEQ ID NO. 18, SEQ ID NO. 19, SEQ ID NO. 20 and analogs.

6. A method for inducing either in vitro or in vivo chemotaxis of fibroblasts and/or inflammatory cells comprising administering to the fibroblasts and/or inflammatory cells at least one peptide of any one of claims 1–5 in an amount effective to induce chemotaxis.

7. A method for inducing or a homolog thereof and a pharmaceutically acceptable carrier proliferation of fibroblasts and/or inflammatory cells comprising administering to the fibroblasts and/or inflammatory cells at least one peptide of any one of claims 1–5 in an amount effective to induce cellular proliferation.

8. A method for inducing either in vitro or in vivo collagen synthesis by fibroblasts comprising administering to the fibroblasts at least one peptide of any one of claims 1–5 in an amount effective to induce collagen synthesis.

9. A method for promoting wound healing in a patient comprising administering to the patient at least one peptide of any one of claims 1–5 in an amount effective to promote wound healing in the patient.

10. A chemotactic peptide consisting of a seven amino acid sequence as set forth in SEQ ID NO. 1.

11. A chemotactic peptide having an amino acid sequence selected from the group consisting of SEQ ID NO. 1, SEQ ID NO. 2, SEQ ID NO. 3, SEQ ID NO. 4 and SEQ ID NO. 5.

12. An analog of a chemotactic peptide set forth in SEQ ID NO. 6 having a cysteine residue attached to the C-terminal end of said peptide.

13. An analog of a chemotactic peptide set forth in any one of claims 1–5 having a cysteine residue attached to the C-terminal or N-terminal end of said peptide.

14. A pharmaceutical composition comprising either a peptide of SEQ ID NO. 1.

* * * * *

UNITED STATES PATENT AND TRADEMARK OFFICE
CERTIFICATE OF CORRECTION

PATENT NO. : 5,436,228
DATED : July 25, 1995
INVENTOR(S) : Postelwaite, et al.

It is certified that error appears in the above-indentified patent and that said Letters Patent is hereby corrected as shown below:

On the Title Page, item 56, under "U.S. PATENT DOCUMENTS", line 4: "Palbdino" should read --Palladino--

On the Title Page, item 56, under "OTHER PUBLICATIONS", line 4: "Margvaudt" should read --Marquardt--

In the Abstract, line 1: "an no " should read --amino--

Column 1. lines 8-11: delete "The invention disclosed herein was made during the course of a grant funded by the United States government and is thus subject to the rights of the government therein" and insert the following: --This invention was made with government support under AR-26034 and AR-39166 awarded by the National Institutes of Health and by a Merit Review Grant awarded by the Veterans Administration. The government has certain rights in the invention--

Column 5, delete lines 17-27 and insert the following:
--Fig. 1A is a graph comparing chemotaxis of fibroblasts in response to peptides 280-339 and 340-391 of TGF-ß.

UNITED STATES PATENT AND TRADEMARK OFFICE
CERTIFICATE OF CORRECTION

PATENT NO. : 5,436,228  
DATED : July 25, 1995  
INVENTOR(S) : Postelwaite, et al.

Page 2 of 5

Figure 1B:
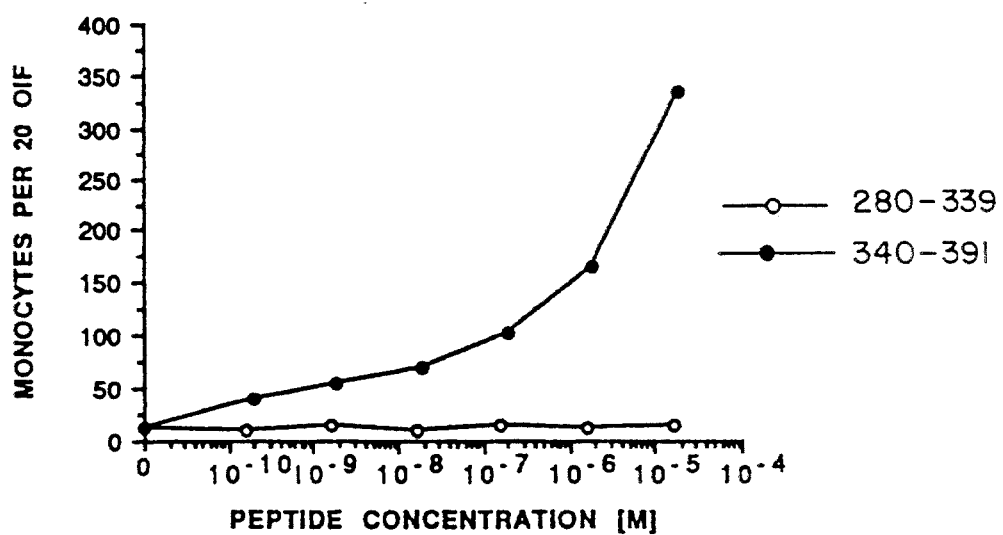

It is certified that error appears in the above-indentified patent and that said Letters Patent is hereby corrected as shown below:

Fig. 1B is a graph comparing chemotaxis of monocytes in response to peptides 280-339 and 340-391 of TGF-ß1.

Figure 1C:
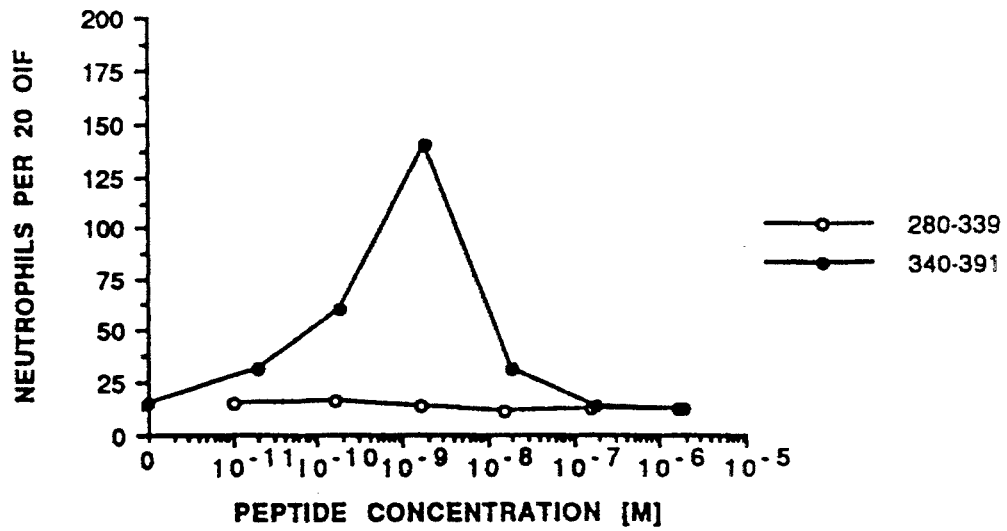

Fig. 1C is a graph comparing chemotaxis of neutrophils in response to peptides 280-339 and 340-391 of TGF-ß1.

Figure 2A:
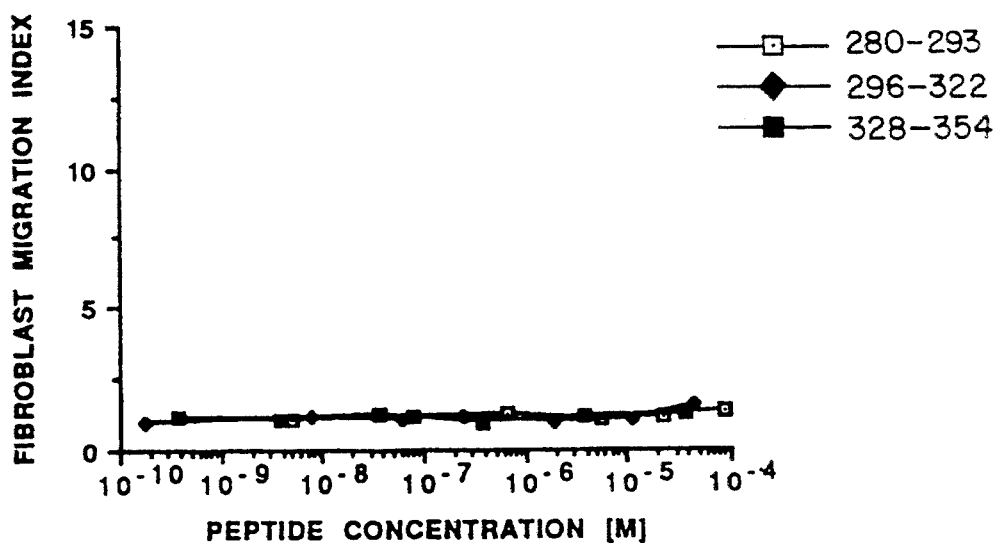
FIG. 2 is a graph showing the chemotactic response of fibroblasts, monocytes and neutrophils to peptides 280–293, 296–322 and 328–354 corresponding to TGF-$\beta$1.

Fig. 2A is a graph showing the chemotactic response of fibroblasts to peptides 280-293, 296-322 and 328-354 of TGF-ß1.

Figure 2B:
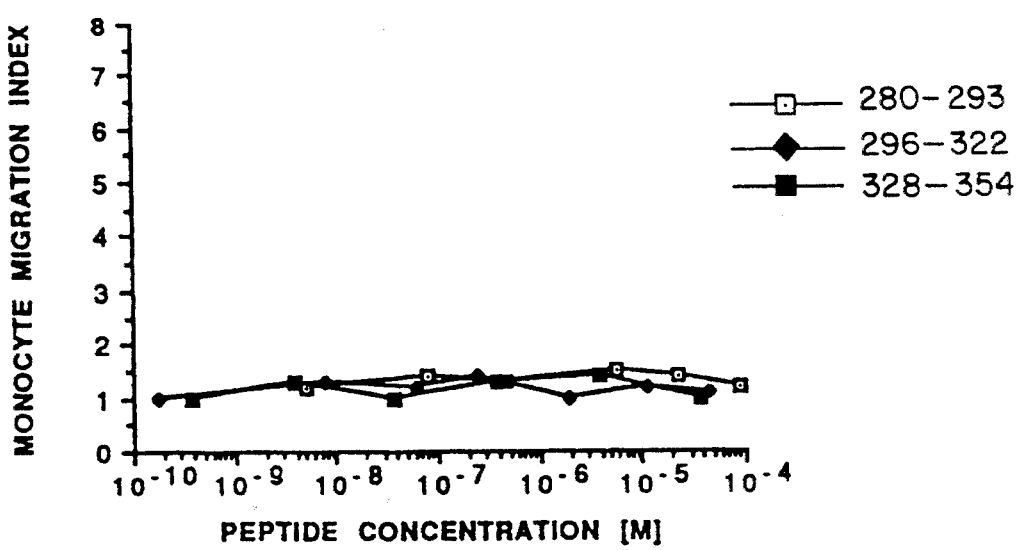

Fig. 2B is a graph showing the chemotactic response of monocytes to peptides 280-293, 296-322 and 328-354 of TGF-ß1.

Figure 2C:
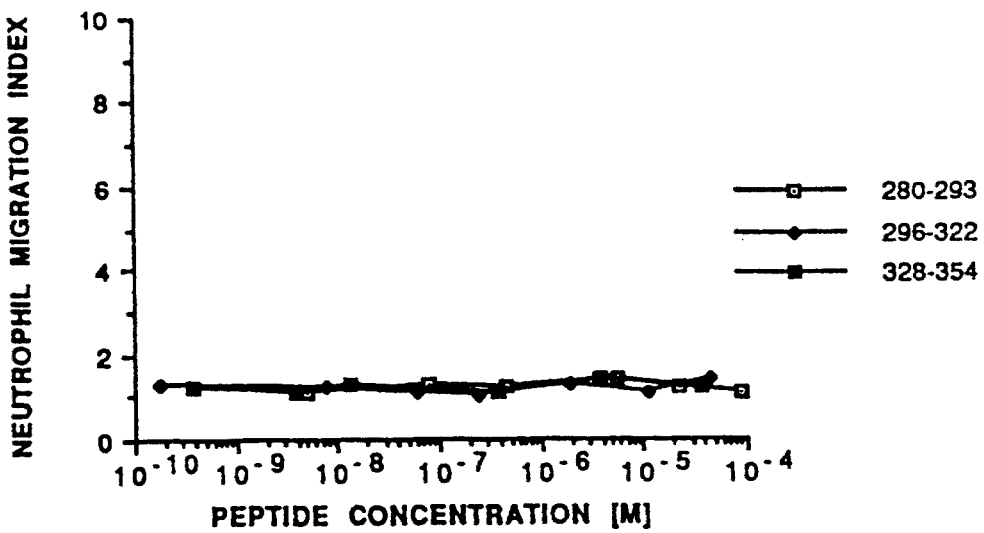

Fig. 2C is a graph showing the chemotactic response of neutrophils to peptides 280-293, 296-322 and 328-354 of TGF-ß1.

Figure 3A:
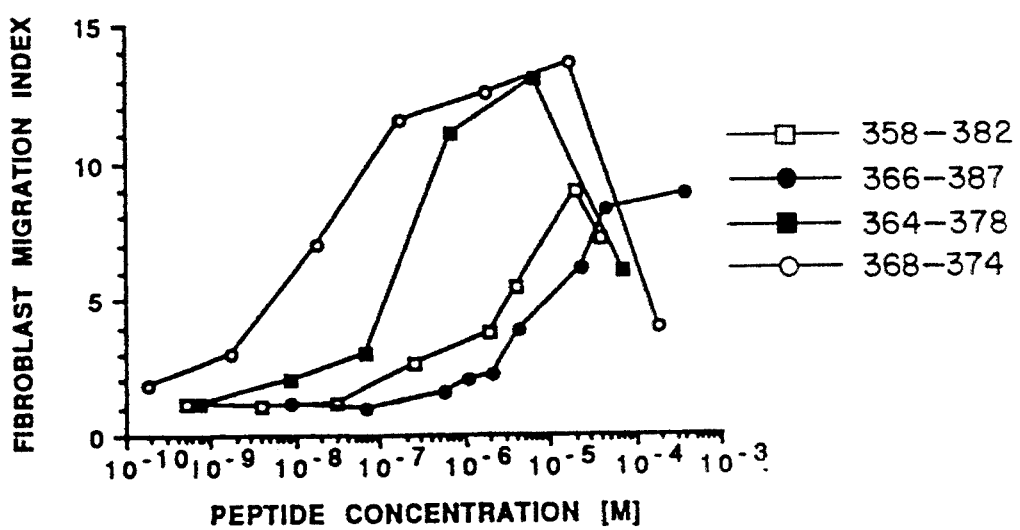
FIG. 3 is a graph showing the chemotactic response of fibroblasts, monocytes and neutrophils to peptides 358–362 (SEQ ID NO. 16), 366–387 (SEQ ID NO. 11), 364–378 (SEQ ID NO. 6) and 368–374 (SEQ ID NO. 1).

Fig. 3A is a graph showing the chemotactic response or fibroblasts to peptides 358-362 (SEQ ID NO. 16), 336-387 (SEQ ID NO. 11), 354-378 (SEQ ID NO. 6) and 368-374 (SEQ ID NO. 1) of TGF-ß1.

UNITED STATES PATENT AND TRADEMARK OFFICE
CERTIFICATE OF CORRECTION

PATENT NO. : 5,436,228
DATED : July 25, 1995
INVENTOR(S) : Postelwaite, et al.

Figure 3B:
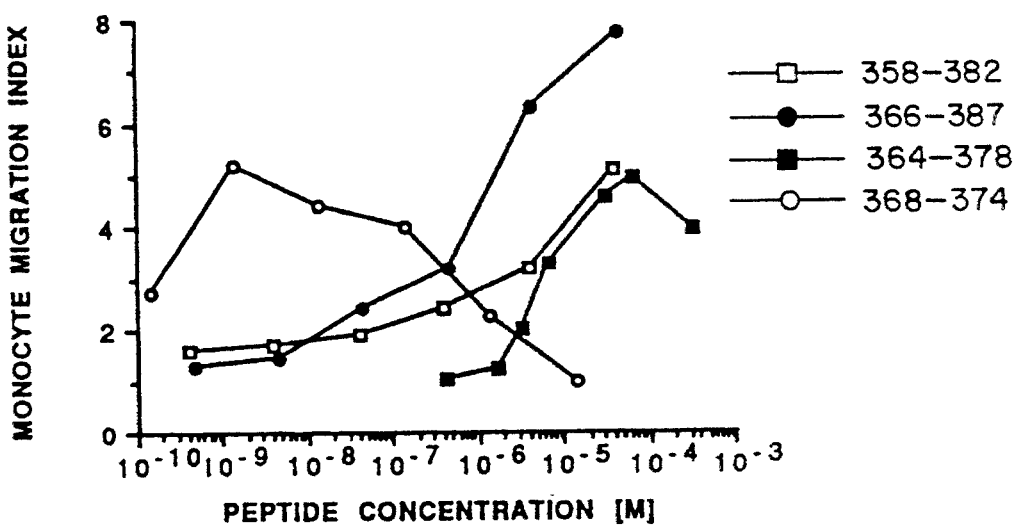

It is certified that error appears in the above-indentified patent and that said Letters Patent is hereby corrected as shown below:

Fig. 3B is a graph showing the chemotactic response of monocytes to peptides 358-362 (SEQ ID NO. 16), 336-387 (SEQ ID NO. 11), 354-378 (SEQ ID NO. 6) and 368-374 (SEQ ID NO. 1) of TGF-ß1.

Figure 3C:
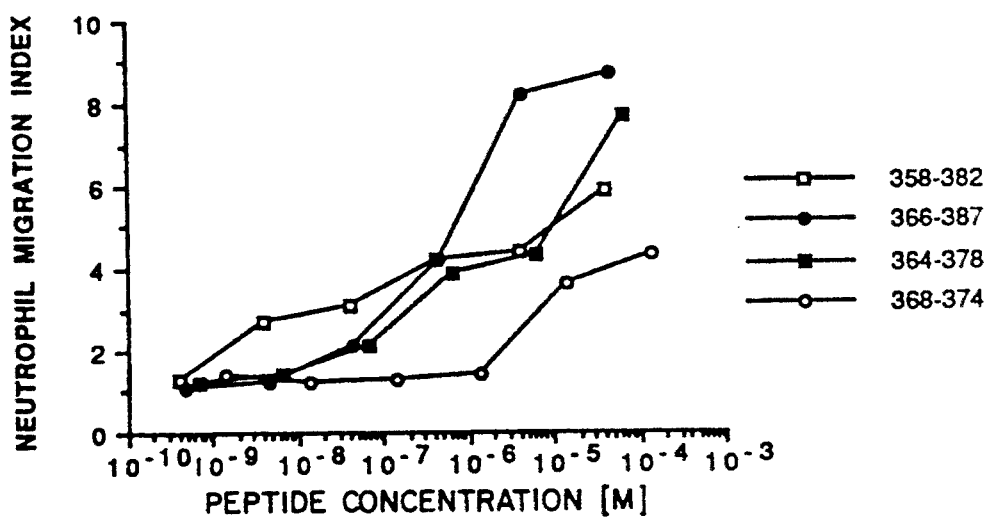

Fig. 3C is a graph showing the chemotactic response of neutrophils to peptides 358-362 (SEQ ID NO. 16), 336-387 (SEQ ID NO. 11), 354-378 (SEQ ID NO. 6) and 368-374 (SEQ ID NO. 1) of TGF-ß1.--

Column 5, lines 29 & 32: "ID NO." should read --ID NOs.--

Figure 11A:
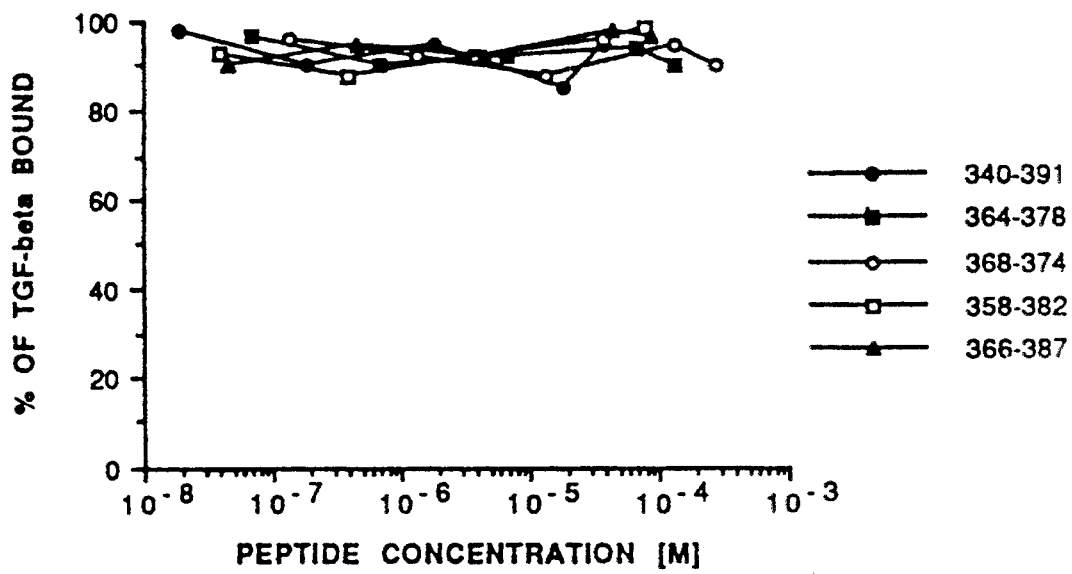
FIG. 11 is a graph depicting competition binding experiments utilizing the peptides of the invention and TGF-$\beta$1.
Figure 11B:
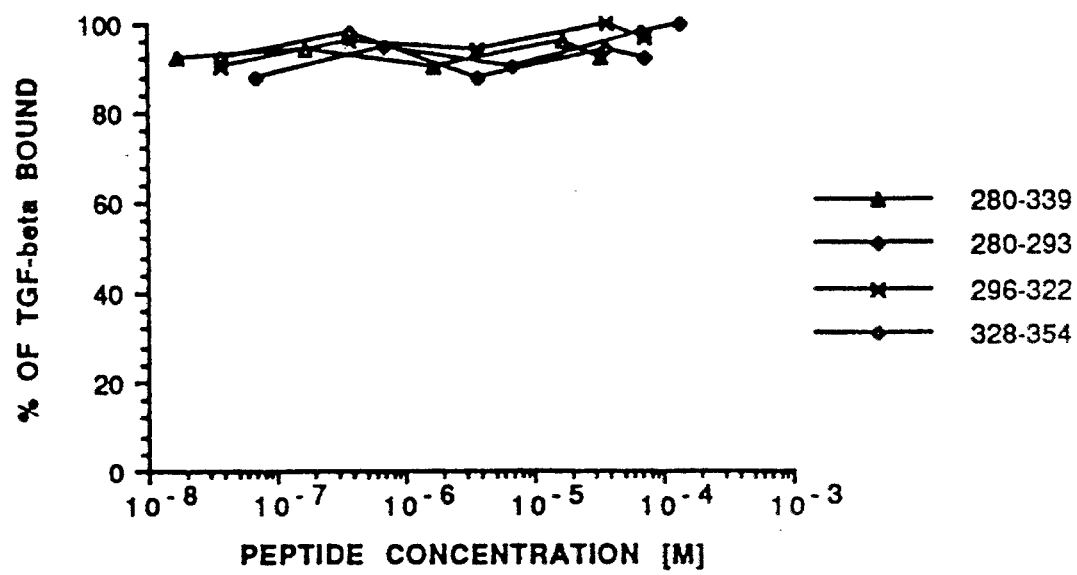

Column 5, line 51: "FIG. 11 is a graph" should read --FIGS. 11A and 11B are graphs--

Column 5, line 58: "Trichone" should read --Trichome--

Column 7, line 2: "(1-25" should read --(1 X 25--

Column 9, line 6: "cells/mi." should read --cells/ml.--

UNITED STATES PATENT AND TRADEMARK OFFICE
CERTIFICATE OF CORRECTION

PATENT NO. : 5,436,228
DATED : July 25, 1995
INVENTOR(S) : Postelwaite, et al.

It is certified that error appears in the above-indentified patent and that said Letters Patent is hereby corrected as shown below:

Column 11, line 23: "ycm" should read --ycpm--

Column 12, line 18: "formationin" should read --formation in--

Column 14, line 30: "FIG. 1," should read --Figures 1A, 1B and 1C,--

Column 15, line 19: "FIG. 2," should read --Figures 2A, 2B and 2C,--

Column 15, line 24: "FIG. 3 demonstrates" should read --Figures 3A, 3B and 3C demonstrate--

Column 19, line 27: "THP-81" should read --THP-1--

Column 19, line 34: "FIG. 11," should read --Figures 11A and 11B,--

Column 29, lines 9-10, Claim 7: delete "or a homolog thereof and a pharmaceutically acceptable carrier" and insert the following: --either in vitro or in vivo--

UNITED STATES PATENT AND TRADEMARK OFFICE
CERTIFICATE OF CORRECTION

PATENT NO. : 5,436,228
DATED : July 25, 1995
INVENTOR(S) : Postelwaite, et al.

It is certified that error appears in the above-indentified patent and that said Letters Patent is hereby corrected as shown below:

Column 30, line 15, Claim 13: after "1-5" insert --or 10-11--

Column 30, line 18, Claim 14: "after "SEQ ID No. 1" insert the following: --or a homolog thereof and a pharmaceutically acceptable carrier--

Signed and Sealed this

Sixteenth Day of April, 1996

BRUCE LEHMAN

Attest:

Attesting Officer

Commissioner of Patents and Trademarks